US010313440B2

(12) United States Patent
Aihara et al.

(10) Patent No.: US 10,313,440 B2
(45) Date of Patent: Jun. 4, 2019

(54) INFORMATION MANAGEMENT SYSTEM, MOBILE COMMUNICATION TERMINAL, DATA BANK DEVICE, SERVICE INFORMATION MANAGEMENT DEVICE, AUTHENTICATION DEVICE, DATA MANAGEMENT METHOD, MOBILE COMMUNICATION TERMINAL CONTROL METHOD, DATABASE CONTROL METHOD, SERVICE INFORMATION MANAGEMENT METHOD, AND PROGRAM

(71) Applicants: GNSS Technologies Inc., Shinjuku-ku, Tokyo (JP); Jichi Medical University, Chiyoda-ku, Tokyo (JP)

(72) Inventors: Masakazu Aihara, Tokyo (JP); Hideyuki Torimoto, Tokyo (JP); Masahiro Asako, Tokyo (JP)

(73) Assignees: GNSS Technologies Inc., Tokyo (JP); Jichi Medical University, Tokyo (JP)

( * ) Notice: Subject to any disclaimer, the term of this patent is extended or adjusted under 35 U.S.C. 154(b) by 332 days.

(21) Appl. No.: 15/037,985

(22) PCT Filed: Nov. 19, 2014

(86) PCT No.: PCT/JP2014/080627
§ 371 (c)(1),
(2) Date: May 19, 2016

(87) PCT Pub. No.: WO2015/076295
PCT Pub. Date: May 28, 2015

(65) Prior Publication Data
US 2016/0308969 A1    Oct. 20, 2016

(30) Foreign Application Priority Data

Nov. 20, 2013  (JP) ................. 2013-240165

(51) Int. Cl.
H04W 24/00    (2009.01)
H04L 29/08    (2006.01)
(Continued)

(52) U.S. Cl.
CPC .......... H04L 67/1097 (2013.01); G06F 16/29 (2019.01); G06F 16/951 (2019.01);
(Continued)

(58) Field of Classification Search
CPC ....... H04L 67/142; H04L 67/12; H04L 67/16; H04W 12/06; H04W 8/245; H04W 4/14;
(Continued)

(56) References Cited

U.S. PATENT DOCUMENTS 6,744,729 B2 * 6/2004 Tinsley ................. G06F 9/451
370/229
9,906,366 B1 * 2/2018 Maria ................... H04L 9/3231
(Continued)

FOREIGN PATENT DOCUMENTS

CN    1930487 A    3/2007
EP    2233943 A1   9/2010
(Continued)

OTHER PUBLICATIONS

Extended European Search Report for Application No. EP 14863163.3, dated Jul. 12, 2017 (6 pages).

Primary Examiner — Danh C Le
(74) Attorney, Agent, or Firm — Nixon Peabody LLP

(57) ABSTRACT

An information management system includes: a mobile communication terminal capable of obtaining location information; and a medical institution provided with a regional medical data bank system and a transmitter. The mobile communication terminal transmits a space-time tag and a terminal ID to the system. The space-time tag is constituted of time information and location information. A space-time
(Continued)

ID information processing unit of the system generates a space-time ID in a folder for each user based on a plurality of space-time tags and stores it in space-time ID information DB. A terminal device of the medical institution transmits the location information of the mobile communication terminal and the time information to the system. A verification processing unit verifies information from the mobile communication terminal against information from a utilization terminal and transmits the information to the utilization terminal when a request for transmission of the information is valid.

16 Claims, 20 Drawing Sheets

(51) Int. Cl.
| | | |
|---|---|---|
| *G06F 16/29* | (2019.01) | |
| *G06F 16/951* | (2019.01) | |
| *G06Q 50/22* | (2018.01) | |
| *G06F 19/00* | (2018.01) | |
| *H04M 1/725* | (2006.01) | |
| *H04W 88/02* | (2009.01) | |

(52) U.S. Cl.
CPC ............ *G06F 19/00* (2013.01); *G06Q 50/22* (2013.01); *H04L 67/32* (2013.01); *H04M 1/72519* (2013.01); *H04M 1/72522* (2013.01); *H04W 88/02* (2013.01)

(58) Field of Classification Search
CPC . H04W 80/04; H04W 88/02; H04M 1/72519; H04M 1/72522
USPC ................................... 455/456.1, 550.1, 418
See application file for complete search history.

(56) References Cited

U.S. PATENT DOCUMENTS

| | | | |
|---|---|---|---|
| 2007/0200756 A1 | 8/2007 | Saito | |
| 2009/0260656 A1* | 10/2009 | Higashijima | ..... H01L 21/31138 134/18 |
| 2010/0131642 A1* | 5/2010 | Chalikouras | ........... G06Q 30/02 709/224 |
| 2011/0016517 A1* | 1/2011 | Kasahara | ................ G01D 4/002 726/7 |
| 2011/0276396 A1* | 11/2011 | Rathod | ............. G06F 17/30867 705/14.49 |
| 2012/0170560 A1* | 7/2012 | Han | ...................... G01S 5/0284 370/338 |
| 2012/0268244 A1 | 10/2012 | Ljung | |
| 2013/0282511 A1* | 10/2013 | Mitchell | ............ G06Q 30/0611 705/26.4 |
| 2014/0122700 A1* | 5/2014 | Jung | ................... H04L 41/5054 709/224 |
| 2016/0036822 A1* | 2/2016 | Kim | .................... H04L 67/1097 726/4 |

FOREIGN PATENT DOCUMENTS

| | | |
|---|---|---|
| EP | 2618182 A1 | 7/2013 |
| JP | 2005-063372 A | 3/2005 |
| JP | 2005/242619 | 9/2005 |
| JP | 2008-072205 A | 3/2008 |
| JP | 2010-282401 A | 12/2010 |
| JP | 2011-258091 A | 12/2011 |
| JP | 2012-216087 A | 11/2012 |
| JP | 5158827 B1 | 3/2013 |
| WO | WO 2005/098462 A1 | 10/2005 |
| WO | WO 2005/098468 A1 | 2/2008 |

* cited by examiner

| ITEM | EXEMPLARY CONTENT |
|---|---|
| 1810 — TIME STAMP | 2013-11-10T12:03:43.035+09:00 |
| 1820 — LATITUDE | 35.676966 |
| 1830 — LONGITUDE | 139.758823 |
| 1840 — URI | http://www.jichi.ac.jp/ehr/d0585958··· |
| 1850 — MIME | video/mpeg |

INFORMATION MANAGEMENT SYSTEM, MOBILE COMMUNICATION TERMINAL, DATA BANK DEVICE, SERVICE INFORMATION MANAGEMENT DEVICE, AUTHENTICATION DEVICE, DATA MANAGEMENT METHOD, MOBILE COMMUNICATION TERMINAL CONTROL METHOD, DATABASE CONTROL METHOD, SERVICE INFORMATION MANAGEMENT METHOD, AND PROGRAM

CROSS-REFERENCE TO RELATED APPLICATIONS

This application is a U.S. national stage of PCT/JP2014/080627, filed on Nov. 19, 2014, which claims priority to Japanese Patent Application No. 2013-240165, filed on Nov. 20, 2013, the contents of which are each incorporated herein by reference in its entirety.

TECHNICAL FIELD

The present disclosure relates to management of information, more particularly, a technique of managing information using location information and time information.

BACKGROUND ART

Conventionally, there has been known a technique of collecting location information of a mobile communication terminal of an individual person over time. For example, Japanese Patent Laying-Open No. 2008-072205 (Patent Document 1) discloses a technique for "accurately specifying an activity of an individual person" (see Abstract). Japanese Patent Laying-Open No. 2005-063372 (Patent Document 2) discloses the following personal activity record storing technique: information is continuously converted into a storable format without human intervention and a large amount of resulting converted information can be accumulated automatically and electronically in such a form that all the information can be referenced while securing privacy" (see Abstract). Japanese Patent Laying-Open No. 2010-282401 (Patent Document 3) discloses a technique for "permitting a service provider to flexibly obtain location information of a user terminal while preventing intensive processing load in a location information management server and appropriately securing the user's privacy" (see Abstract).

CITATION LIST

Patent Document

PTD 1: Japanese Patent Laying-Open No. 2008-072205
PTD 2: Japanese Patent Laying-Open No. 2005-063372
PTD 3: Japanese Patent Laying-Open No. 2010-282401

SUMMARY OF INVENTION

Technical Problem

Among industries for providing services to individual people, for example, in a medical industry, a strong demand arises with regard to increase in efficiency of medical diagnosis and other medical services and improvement in patients' convenience by sharing medical diagnosis information and service information among medical institutes. At present, however, medical information and service information are managed by way of patients' identification codes (ID: Identification) individually given by respective medical institutions or nursing care service organizations. Furthermore, pieces of sensor information output from monitors and other various sensors may be managed using individual device identification codes given for respective systems to which the sensors belong. This makes it difficult to achieve commonality among pieces of medical information and service information associated with various patients' identification codes and device identification codes.

Meanwhile, a common identification code for sharing only medical information or the like is taken into consideration. Such medical information may include, for example, health data indicating a health condition of an individual person. The health data, in particular, health data of an elderly person can be used for not only a medical institution but also a nursing care service, an insurance service, and other peripheral services, and are therefore desirably used by the other services. Moreover, with progression of information communication networks, information obtained from various types of monitors, sensors and other information obtaining devices are desirably shared as required. Accordingly, a technique for efficiently managing identification information and various types of other information is required. Also, a technique for authenticating an activity of an individual person is required.

The present disclosure has been made in consideration of the background described above. An object in a certain aspect thereof is to provide an information management system capable of sharing information. An object in another aspect is to provide an information management system capable of identifying an activity of an individual person. An object in another aspect is to provide a mobile communication terminal for generating sharable information. An object in another aspect is to provide a mobile communication terminal capable of generating information with which an activity of an individual person can be authenticated. An object in another aspect is to provide a data bank device capable of sharing information of an individual person. An object in another aspect is to provide a service information management device for managing sharable service information.

An object in another aspect is to provide a user data management method. An object in another aspect is to provide a method for controlling a mobile communication terminal to generate sharable user data. An object in another aspect is to provide a method for controlling a database for managing sharable user data. An object in another aspect is to provide a method for controlling a service information management device that manages sharable service information to be provided to a user.

Further, an object in another aspect is to provide a program for causing a computer to perform one of the above methods.

Solution to Problem

An information management system according to one embodiment includes: a plurality of mobile communication terminals each capable of obtaining location information; a data bank device for managing a database of each user of the plurality of mobile communication terminals; and a service information management device for transmitting service information to the data bank device, the service information being associated with a service provided to a user of a specific mobile communication terminal of the plurality of mobile communication terminals. Each of the mobile communication terminals includes: an obtaining unit configured to obtain identification information including a set of location information for specifying a location of the mobile communication terminal and time information; and a first transmitting unit configured to transmit a plurality of pieces of the identification information to the data bank device and the service information management device. The service information management device includes: a receiving unit configured to receive the identification information from the specific mobile communication terminal; and a second transmitting unit configured to transmit, to the data bank device, the service information and identification information received from the specific mobile communication terminal. The data bank device includes: a receiving unit configured to receive the identification information transmitted by each of the plurality of mobile communication terminals and the identification information and service information transmitted by the service information management device; and a verifying unit configured to verify each piece of the received identification information to specify a user having been provided with a service associated with the service information.

Preferably, in the mobile communication terminal, the obtaining unit includes: a first positioning unit configured to obtain location information of the mobile communication terminal and time based on respective positioning signals transmitted from a plurality of positioning satellites; and a second positioning unit configured to receive a signal including location information indicating a location of a location information transmitting device from the location information transmitting device, extract the location information from the received signal, and obtain time associated with the location information, the location information transmitting device being capable of transmitting a signal in a same format as a format of each of the positioning signals transmitted from the plurality of positioning satellites.

Preferably, from a device other than the location information transmitting device, the second positioning unit is configured to obtain the time associated with the location information extracted by the second positioning unit.

Preferably, the information management system further includes an authentication device for authenticating the identification information obtained by each of the mobile communication terminals. The authentication device includes: a receiving unit configured to receive, from each of the mobile communication terminals, the location information extracted by the second positioning unit; a determining unit configured to check whether or not the received location information is valid location information; and a time adding unit configured to, when the received location information is valid location information, add time information to the location information received from each of the mobile communication terminals and return the location information having the time information added thereto to the mobile communication terminal having transmitted the location information.

Preferably, the first transmitting unit is configured to transmit the identification information to the service information management device based on approval by the user of the mobile communication terminal.

Preferably, the obtaining unit is configured to obtain a plurality of pieces of the location information at a predetermined interval.

Preferably, the obtaining unit is configured to obtain the location information when the mobile communication terminal is present in a range registered in advance.

According to another embodiment, a mobile communication terminal is provided. The mobile communication terminal includes: an obtaining unit configured to obtain identification information including a set of location information for specifying a location of the mobile communication terminal and time information; and a transmitting unit configured to transmit a plurality of pieces of the identification information to a data bank device for managing a database of a user of the mobile communication terminal and to a service information management device for transmitting, to the data bank device, service information associated with a service provided to the user.

Preferably, the obtaining unit includes: a first positioning unit configured to obtain location information of the mobile communication terminal and time based on respective positioning signals transmitted from a plurality of positioning satellites; and a second positioning unit configured to receive a signal including location information indicating a location of a location information transmitting device from the location information transmitting device, extract the location information from the received signal, and obtain time associated with the location information, the location information transmitting device being capable of transmitting a signal in a same format as a format of each of the positioning signals transmitted from the plurality of positioning satellites.

Preferably, the transmitting unit is configured to transmit the identification information to the service information management device based on approval by the user of the mobile communication terminal.

Preferably, the obtaining unit is configured to obtain a plurality of pieces of the location information at a predetermined interval.

Preferably, when the mobile communication terminal is present in a range registered in advance, the obtaining unit is configured to obtain the location information.

According to another embodiment, there is provided a data bank device for managing a database of each user of a plurality of mobile communication terminals. The data bank device includes: a receiving unit configured to receive identification information from each of the plurality of mobile communication terminals and receive the identification information from a service information management device for transmitting service information to the data bank device, the identification information including a set of location information for specifying a location of the mobile communication terminal and time information, the service information being associated with a service provided to a user of a specific mobile communication terminal of the plurality of mobile communication terminals; and a verifying unit configured to verify each piece of the received identification information to specify the user having been provided with the service associated with the service information.

According to another embodiment, a service information management device is provided. The service information management device includes: a receiving unit configured to receive identification information including a set of location information and time information from a mobile communication terminal capable of obtaining the location information; and a transmitting unit configured to transmit service information to a data bank device for managing a database of a user of the mobile communication terminal, the service information being associated with a service provided to the user of the mobile communication terminal.

According to another embodiment, an authentication device for authenticating location information is provided.

The authentication device includes: a receiving unit configured to receive location information transmitted by a location information transmitting device capable of transmitting a signal in a same format as a format of each of positioning signals transmitted from a plurality of positioning satellites; a checking unit configured to check whether or not the location information is valid; and a transmitting unit configured to, when the location information is valid, add, to the location information, information indicating that the location information is valid and transmit the location information having the information added thereto to the location information transmitting device.

Preferably, the information indicating that the location information is valid includes time information.

According to another embodiment, a data management method is provided. The management method includes the steps of: obtaining identification information for each of a plurality of mobile communication terminals each capable of obtaining location information, the identification information including a set of location information for specifying a location of the mobile communication terminal and time information; transmitting the identification information to a data bank device for managing a database of each user of the plurality of mobile communication terminals and to a service information management device for transmitting, to the data bank device, service information associated with a service provided to each user of the plurality of mobile communication terminals; receiving identification information of each of the mobile communication terminals; transmitting, to the data bank device, (i) service information associated with a service provided to a user of a specific mobile communication terminal of the plurality of mobile communication terminals and (ii) the identification information received from each of the plurality of mobile communication terminals; receiving identification information transmitted by the specific mobile communication terminal; and comparing the identification information received from the specific mobile communication terminal with the identification information transmitted by the service information management device.

According to another embodiment, a mobile communication terminal control method is provided. The method includes the steps of: obtaining identification information including a set of location information for specifying a location of the mobile communication terminal and time information; and transmitting the identification information to a data bank device for managing a database of a user of the mobile communication terminal and to a service information management device for transmitting, to the data bank device, service information associated with a service provided to the user.

According to another embodiment, there is provided a method for managing a database of each user of a plurality of mobile communication terminals. The method includes the steps of: receiving identification information from each of the plurality of mobile communication terminals and receiving the identification information from a service information management device for transmitting service information to the data bank device, the identification information including a set of location information for specifying a location of the mobile communication terminal and time information, the service information being associated with a service provided to a user of a specific mobile communication terminal of the plurality of mobile communication terminals; and verifying each piece of the received identification information to specify a user having been provided with a service associated with the service information.

According to another embodiment, a service information management method is provided. The method includes the steps of: receiving identification information from a mobile communication terminal capable of obtaining location information, the identification information including a set of location information of the mobile communication terminal and time information; and transmitting service information to a data bank device for managing a database of a user of the mobile communication terminal, the service information being associated with a service provided to the user of the mobile communication terminal.

According to another embodiment, there is provided a program for causing a computer to execute any one of the methods recited above.

The foregoing and other objects, features, aspects and advantages of the present invention will become more apparent from the following detailed description of the present invention when taken in conjunction with the accompanying drawings.

BRIEF DESCRIPTION OF DRAWINGS

FIG. 18 shows an exemplary space-time tag 181 in a certain aspect.

DESCRIPTION OF EMBODIMENTS

Figure 1:
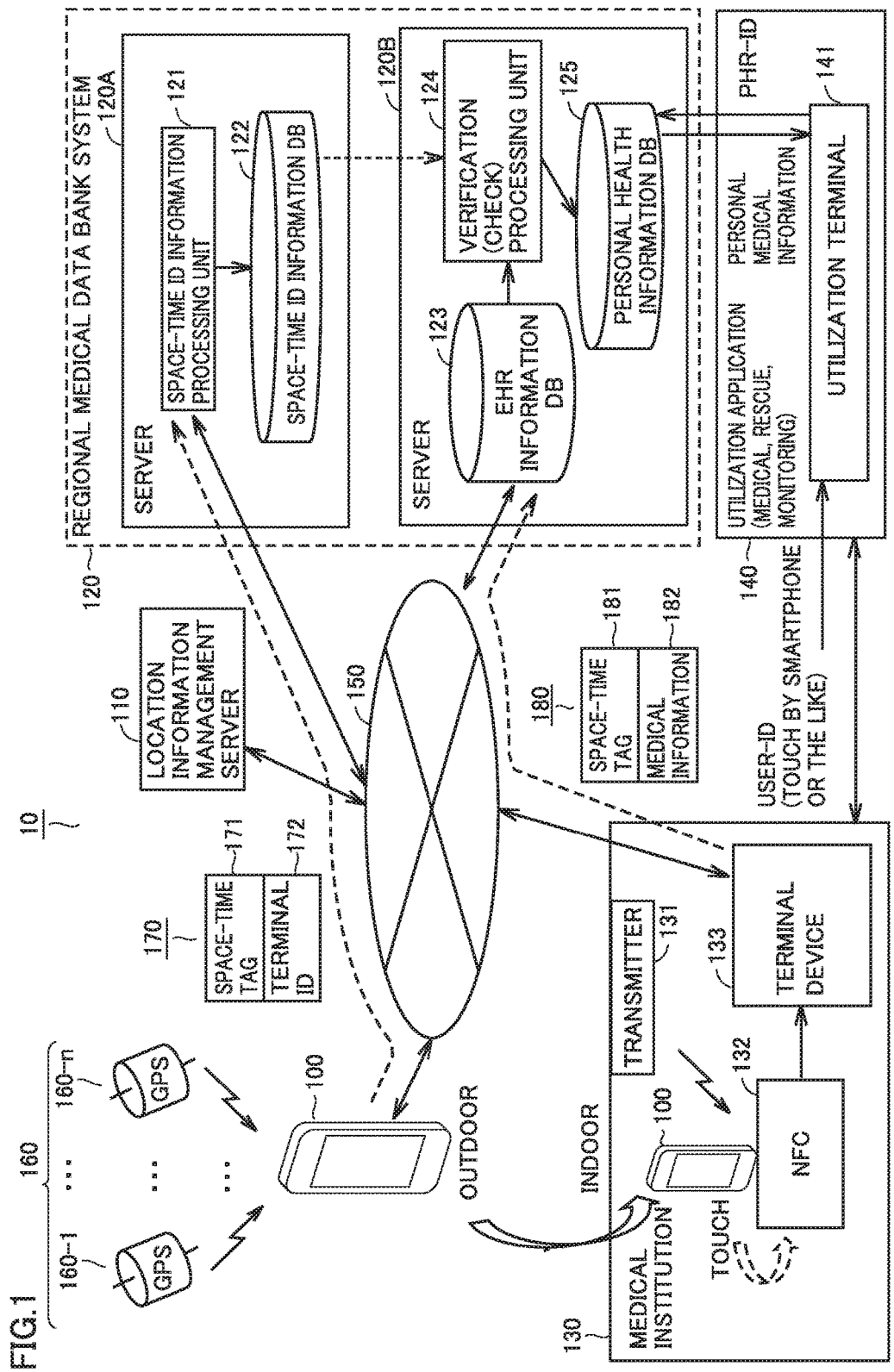
FIG. 1 shows an overview of a configuration of an information management system 10 according to an embodiment of the present invention.

The following describes embodiments of the present invention with reference to figures. In the description below, the same components are given the same reference characters. Their names and functions are also the same. Therefore, detailed description thereof will not be repeated.

[Configuration of Information Management System]

With reference to FIG. 1, the following describes an information management system 10 according to the present embodiment. FIG. 1 shows an overview of a configuration of information management system 10 according to the embodiment of the present invention. In a certain aspect, information management system 10 includes a mobile communication terminal 100, a regional medical data bank system 120, and a terminal device 133.

Mobile communication terminal 100 receives positioning signals sent from GPS (Global Positioning System) satellites 160-1 to 160-*n* (when indicated collectively, they will be referred to as "GPS satellite 160"), and can specify the location of mobile communication terminal 100 based on the respective positioning signals. Moreover, mobile communication terminal 100, which can be connected to a network 150, can transmit information to a different information communication device or receive information from a different information communication device via network 150. For example, mobile communication terminal 100 can be connected to a location information management server 110 or regional medical data bank system 120 via the Internet. Regional medical data bank system 120 includes a server 120A and a server 120B.

In a certain aspect, mobile communication terminal 100 functions as a PHR (Personal Health Record) card. In the present embodiment, PHR represents insurance-related information of a patient, who is the user of the PHR card. For example, PHR includes the height, weight, blood type, vital information, allergies, side effects from medicines, anamnesis, disease symptom, prescription, medication and the like about the patient, but can include other information. In the present embodiment, the PHR card is a portable communication device having a location information obtaining function, a communication function, and an information processing function. Examples of the PHR card may include a smartphone, an IC (Integrated Circuit) card, a bracelet, and the like. The PHR card provides an indication of the patient's condition when he/she visits a hospital or is hospitalized. Moreover, even if the patient falls down to the ground in the hospital or on a street, the PHR card provides a notification of the location and condition of the patient to his/her personal doctor or a terminal for diagnosis. Moreover, if a region in which the user of the PHR card is present is affected by a disaster, the PHR card can present disaster information to support guiding the user to escape.

Mobile communication terminal 100 regularly generates space-time tags. More specifically, as a space-time tag, mobile communication terminal 100 obtains location information and time information indicating time at which the location information has been obtained. The timing of obtainment can be varied depending on a type of service provided to mobile communication terminal 100. The location information of mobile communication terminal 100 is authenticated in location information management server 110 and mobile communication terminal 100 transmits, to regional medical data bank system 120, the space-time tag including the authenticated location information.

It should be noted that, for example, the location information can be used based on mesh data as a unit. The mesh data represents a regional mesh determined as a latitude/longitude location square on a map in order to digitize information on the map or obtain various types of statistical information. For example, when a specific location is specified by location information, a regional mesh including the location information is specified. Hence, when one wishes to know a user who was in the regional mesh during a certain period, such a user can be extracted by designating the period and the location information.

A location information management server 110 is connected to network 150. Location information management server 110 is implemented by a computer having a well-known configuration, for example. In a certain aspect, based on a signal sent from mobile communication terminal 100, location information management server 110 authenticates whether or not the information indicating the location of mobile communication terminal 100 is valid. When the information indicating that the location is valid, location information management server 110 provides an authentication result indicating that the location information of mobile communication terminal 100 is valid. For example, when mobile communication terminal 100 and location information management server 110 have a satellite positioning function, the time of mobile communication terminal 100 and the time of location information management server 110 are synchronized with each other. Hence, the time information indicating the time at which the valid location information has been obtained is valid time information. Thus, a set of such location information and time information can constitute a space-time tag.

In a certain aspect, respective clocks of devices included in information management system 10 are preferably synchronized with one another. In this case, the time line of a space-time tag accumulated in regional medical data bank system 120 matches with the time line of a space-time tag sent from mobile communication terminal 100, thereby preventing an error in extracting data using a space-time tag. The synchronization of clocks is implemented using time information included in a signal sent from GPS satellite 160, for example.

In regional medical data bank system 120, server 120A and server 120B are both connected to network 150. Server 120A includes a space-time ID information processing unit 121 and a space-time ID information DB (database) 122. Server 120B includes an EHR (Electronic Health Record) information DB 123, a verification (check) processing unit 124, and a personal health information DB 125. Each of server 120A and server 120B is implemented using a computer device having a well-known configuration. Server 120A and server 120B are connected to each other via a switch (not shown) when verification (check) processing unit 124 performs a process. The switch is operated when, for example, a command to server 120A and server 120B is provided; however, a trigger for operating the switch is not limited to this.

Space-time ID information processing unit 121 accumulates, in space-time ID information DB 122, space-time tags (location information+time information) sent from mobile communication terminal 100. A folder, in which the space-time tags are accumulated, is prepared for each user who uses the service of regional medical data bank system 120. Hence, for example, when personal information of a user such as medical information is requested, a plurality of space-time tags stored in the folder of the user specified by terminal identification information will be a target for search.

EHR information DB 123 holds electronic health records (EHR). An electronic health record includes health and medical information or the like of an individual person as sent from medical institution 130 or other medical institutions. EHR information DB 123 is configured to be capable of sharing health and medical information (such as electronic medical records) among medical institutions in a region. Such health and medical information has been used in an isolated manner in each medical institution.

Personal health information DB 125 holds health and medical information (PHR) over the entire life of each individual person. Hence, when an institution requests the health and medical information of the individual person and the individual person agrees to provide it thereto, the institution can obtain the health and medical information from personal health information DB 125.

Terminal device 133 is connected to network 150. Terminal device 133 is installed in a hospital or another medical institution 130. The location information of medical institution 130 itself can be specified by an ID assigned thereto, for example. Such IDs are assigned to respective medical institutions and other institutions by an administration authority. Terminal device 133 and regional medical data bank system 120 are connected to each other via a dedicated line, for example. Medical institution 130 further includes a transmitter 131. At a location to which a positioning signal sent by GPS satellite 160 is not propagated, such as an indoor location or a location between high-rise buildings, transmitter 131 transmits a signal having a configuration similar to that of the positioning signal. In a certain aspect, transmitter 131 is implemented as an indoor transmitter also referred to as "IMES (Indoor Messaging System) transmitter", for example. The signal includes information indicating the location of transmitter 131. It should be noted that the information indicating the location is not limited to geographic coordinates such as latitude, longitude, and altitude, and may include a floor ID (Identification), an RF (Radio Frequency) tag, and the like. Moreover, the geographic coordinates are not limited to those illustrated above, and may be based on any coordinate system included in the geographic coordinates system.

A signal sent from one transmitter 131 includes information with which the location can be specified. In the case where the signal sent from transmitter 131 has the same configuration as that of the positioning signal and mobile communication terminal 100 has a location information obtaining function for detecting the signal from transmitter 131, mobile communication terminal 100 can detect the location of transmitter 131 as the location of mobile communication terminal 100 by receiving the signal from transmitter 131 even if the signal from GPS satellite 160 cannot be received.

An NFC terminal 132, which has an NFC (Near Field Communication) function, is connected to terminal device 133. NFC terminal 132 can communicate with mobile communication terminal 100 and other communication terminals having the NFC function. When NFC terminal 132 detects touch by mobile communication terminal 100, NFC terminal 132 requests mobile communication terminal 100 for (i) the terminal identification information of mobile communication terminal 100 or (ii) service identification information for identifying a service provided by medical institution 130 in which NFC terminal 132 is provided. The service identification information identifies a service based on a type of medical treatment (such as surgery or internal medicine) received by the user as a patient in medical institution 130. In response to the request, mobile communication terminal 100 displays a screen on a monitor of mobile communication terminal 100 so as to make an inquiry as to whether to permit to transmit the terminal identification information and the service identification information to NFC terminal 132. When the user of mobile communication terminal 100 touches the monitor to approve to transmit the information to NFC terminal 132, mobile communication terminal 100 transmits the terminal identification information and the service identification information to NFC terminal 132. NFC terminal 132 receives the terminal identification information and the service identification information from mobile communication terminal 100 and transmits them to terminal device 133. It should be noted that the manner of communication with mobile communication terminal 100 is not limited to the NFC technique, and infrared communication, Bluetooth®, and other short-distance communication techniques may be used therefor.

Terminal device 133 transmits information obtained in medical institution 130, to regional medical data bank system 120 via network 150. Information 180 transmitted includes a space-time tag 181 and medical information 182, for example. Medical information 182 is information indicating details of medical practice in medical institution 130, prescription, and the like, for example. The configuration of space-time tag 181 will be described later.

When approved by the user of mobile communication terminal 100, terminal device 133 transmits, to server 120B, the medical information indicating medical practice, prescription, and the like provided on that occasion. Hence, it can be said that the space-time ID and medical information stored in EHR information DB 123 are data generated in an event-driven manner. Meanwhile, mobile communication terminal 100 transmits information 170 to regional medical data bank system 120 regularly. Hence, the space-time tag stored in space-time ID information DB 122 is not completely the same as the space-time tag stored in EHR information DB 123.

In a certain aspect, terminal device 133 can communicate with a utilization application 140. Utilization application 140 includes an utilization terminal 141. Utilization terminal 141 has the NFC function, for example. Utilization terminal 141 is implemented by a computer having a well-known configuration, for example. Utilization application 140 includes an entity employing medical information, such as a public administration, a medical institution, a rescue institution, or a nursing care service provider.

In utilization application 140, utilization terminal 141 receives medical information of an individual person from personal health information DB 125 of regional medical data bank system 120. Moreover, in another aspect, utilization terminal 141 of utilization application 140 transmits PHR (Personal Health Record)-ID to personal health information DB 125 of regional medical data bank system 120.

Information 170 transmitted from mobile communication terminal 100 to regional medical data bank system 120 includes space-time tag 171 and terminal ID 172. In a certain aspect, space-time tag 171 may include: time information obtained upon satellite positioning or time information provided by location information management server 110; and location information obtained by positioning employing a signal from each GPS satellite 160 or location information sent from a location information transmitter (for example, transmitter 131). Terminal ID 172 includes a terminal identification number included in a SIM (Subscriber Identity Module) card, for example. Hence, for example, even if user authentication employing space-time tag 171 fails, the user can be identified using the terminal identification number.

[Technical Idea]

Figure 2:
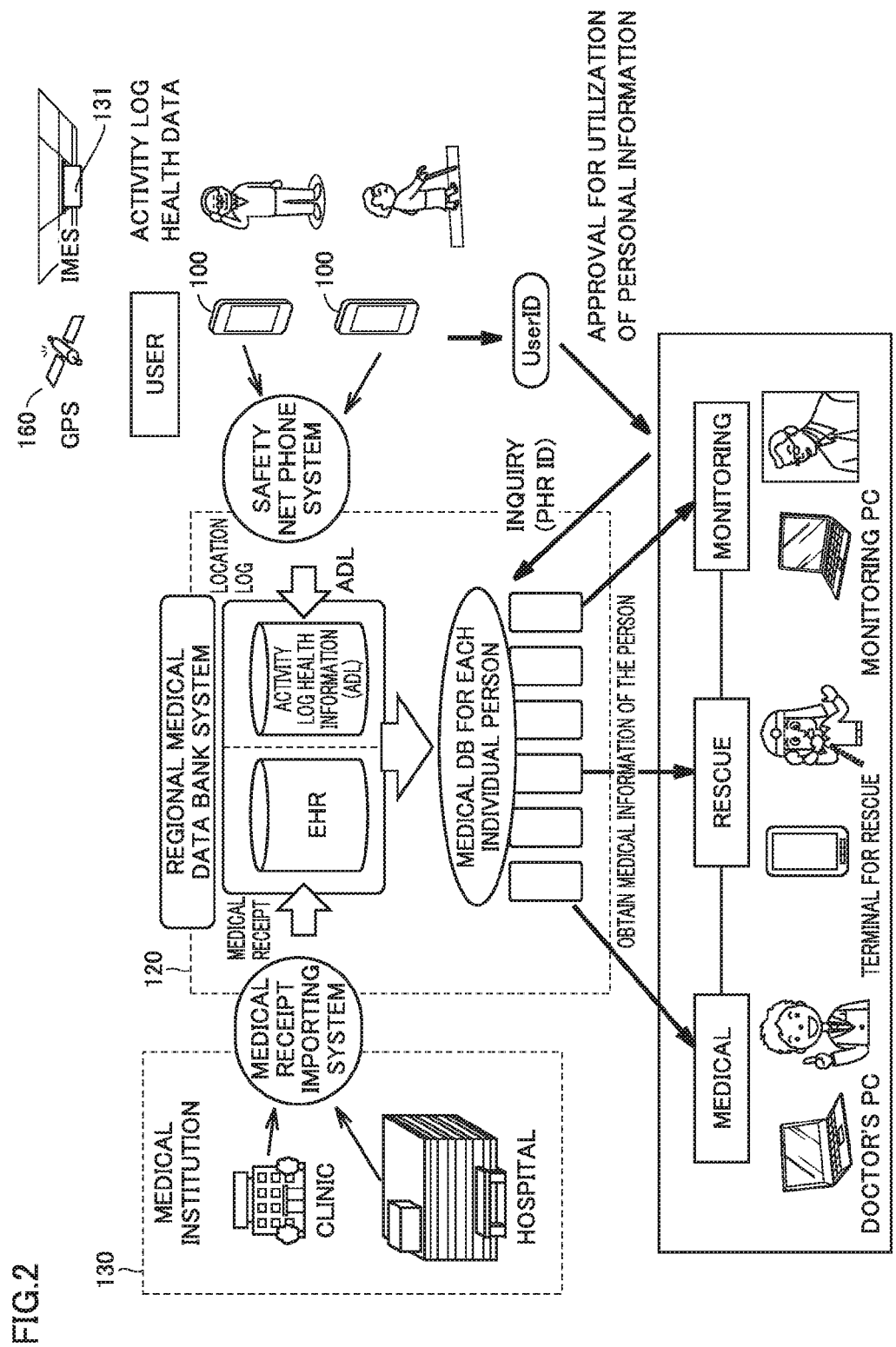
FIG. 2 shows an overview of a configuration of a system to which a technical idea according to the present invention is applied.

With reference to FIG. 2, the following further describes a technical idea according to the present embodiment. FIG. 2 shows an overview of a configuration of a system to which the technical idea according to the present invention is applied. In a certain aspect, regional medical data bank system 120 is connected to medical institution 130 via a medical receipt importing system. For example, information obtained in a clinic or hospital is sent to regional medical data bank system 120 via the medical receipt importing system. Regional medical data bank system 120 holds, in EHR information DB 123 or anothr database, the data obtained via the medical receipt importing system.

Regional medical data bank system 120 is also connected to mobile communication terminal 100 via a safety net phone system or other information communication systems. In the present embodiment, the safety net phone system is one form of a so-called monitoring service, and is a service provided by a health management center to residents living alone. For example, each of such residents living alone has mobile communication terminal 100. The resident operates mobile communication terminal 100 to transmit his/her health condition to the health management center. When the health management center detects a resident who has not reported it, the health management center makes a phone call to mobile communication terminal 100 or land-line telephone of the resident for the purpose of safety check and urges the resident to report his/her health condition. An example of mobile communication terminal 100 is a smartphone readily handled by elderly people, but other mobile communication terminals may be used. Moreover, in the present embodiment, the user of mobile communication terminal 100 is not limited to elderly people as long as the user is a user of medical institution 130 (for example, a patient, a care worker, an assistant, or the like).

Mobile communication terminal 100 transmits an activity log and health data to regional medical data bank system 120 via the safety net phone system. The activity log indicates a record of activities of an elderly person, and the health data indicates his/her health condition. In regional medical data bank system 120, the activity log and health data of the elderly person are stored in an activity log health information DB as information of Activities of Daily Living (ADL). In regional medical data bank system 120, a medical DB is held for each individual person. The medical DB for each individual person includes data obtained from the EHR information DB or the activity log health information DB.

In a certain aspect, mobile communication terminal 100 held by the elderly person outputs the user ID in response to an operation thereon. The user ID thus output is received by a PC or another information communication terminal owned by a doctor, a rescuer, a monitoring service provider, or the like, for example. This information communication terminal employs the received user ID to make an inquiry (PHR ID) to regional medical data bank system 120. Regional medical data bank system 120 determines whether or not the inquiry is a valid inquiry. When it is a valid inquiry, regional medical data bank system 120 reads information, for which the inquiry has been made, from the medical DB for the individual person, and transmits the information to the sender of the inquiry.

[Location Information Providing System]

Figure 3:
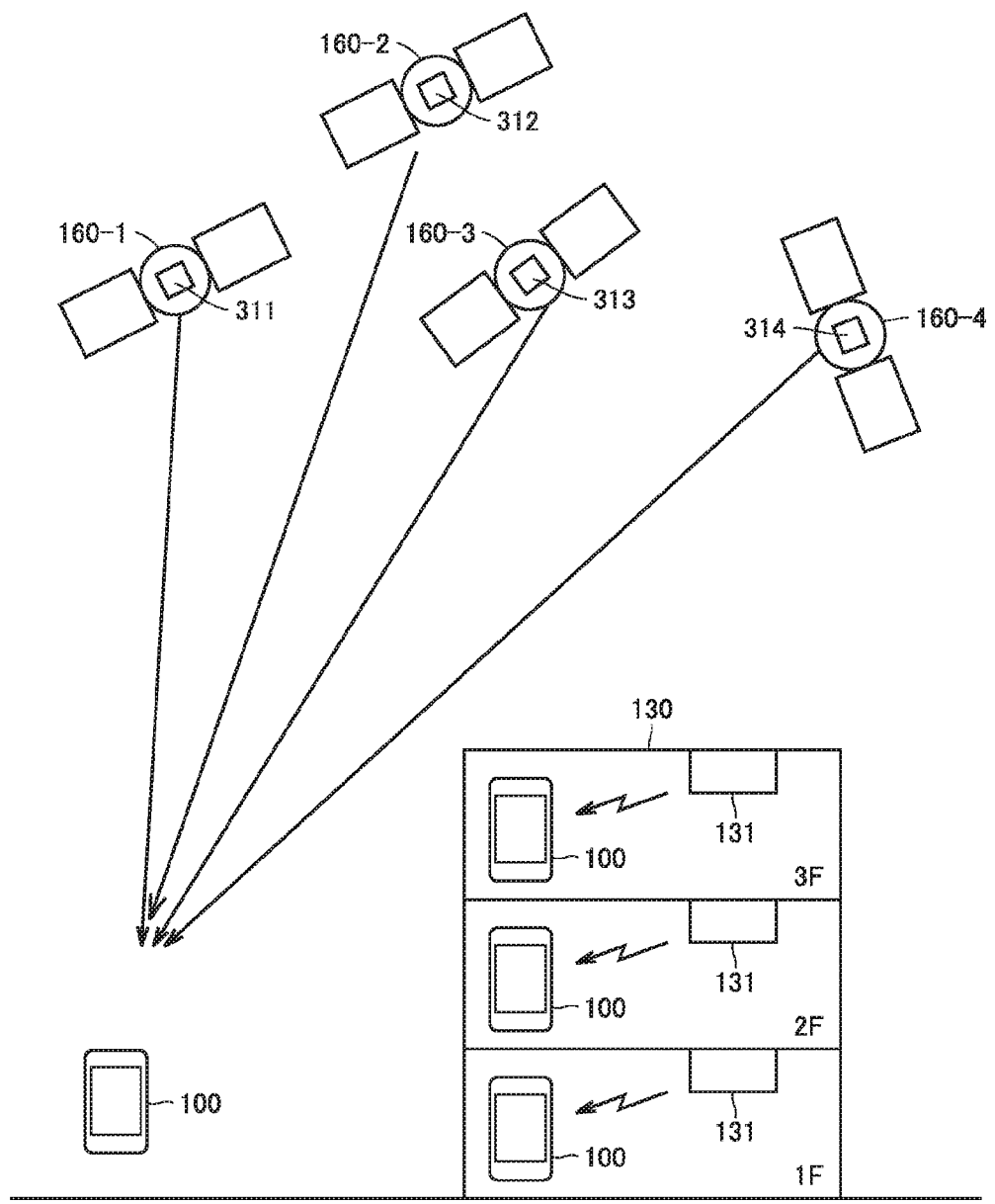
FIG. 3 shows a configuration of a location information providing system.

Here, with reference to FIG. 3, the following describes a location information providing system, which is one form of a structure for providing location information in the embodiment of the present invention. FIG. 3 shows a configuration of the location information providing system. The location information providing system includes: GPS satellites 160-1, 160-2, 160-3, 160-4 flying at an altitude of about 20,000 m above the ground and emitting signals for positioning (hereinafter, referred to as "positioning signals"); and mobile communication terminals 100-1 to 100-4 functioning as devices for providing location information. When collectively mentioned, mobile communication terminals 100-1 to 100-4 will be referred to as "mobile communication terminal 100". Mobile communication terminal 100 is a terminal having the satellite positioning function, such as a mobile phone, a smartphone, a portable navigation system and other portable positioning devices.

The positioning signal is a so-called spread spectrum signal and, by way of example, it is a GPS signal. The positioning signal, however, is not limited to the GPS signal. It should be noted that for ease of explanation, the GPS will be described below as an example of the positioning system, but the technical idea according to the location information providing system is applicable to other satellite positioning systems (such as Galileo from the Europe and GLONASS (Global Navigation Satellite System) developed by the former Soviet Union).

The center frequency of the positioning signal is, for example, 1575.42 MHz but the present invention is not limited to this. The spreading frequency of the positioning signal is, for example, 1.023 MHz but the present invention is not limited to this. Here, the frequency of the positioning signal becomes the same as that of a C/A (Coarse and Access) signal in a L1 band of the existing GPS. Accordingly, an existing positioning signal receiving circuit (such as a GPS signal receiving circuit) can be used, whereby mobile communication terminal 100 can receive a positioning signal without adding a new circuit.

The positioning signal may be modulated with a rectangular wave of 1.023 MHz. In that case, if the data channel of the modulated signal is the same as that of the positioning signal planned for new transmission in the L1 band, the user can receive the positioning signal using a receiver that can receive and process the new GPS signal. It should be noted that the frequency of the rectangular wave is not limited to 1.023 MHz. The frequency for modulation can be determined based on a trade-off with spectrum separation for avoiding interference with an existing C/A signal and/or other signals.

GPS satellite 160-1 has a transmitter 311 mounted thereon, for emitting the positioning signal. Likewise, GPS satellites 160-2, 160-3, 160-4 respectively have transmitters 312, 313, 314 mounted thereon and each having the same function. Mobile communication terminals 100-2, 100-3, 100-4 having the same function as that of mobile communication terminal 100-1 can be used even in medical institution 130 or other locations which electric waves are less likely to reach. On a ceiling of the first floor of medical institution 130, transmitter 131 is installed. Mobile communication terminal 100-4 receives a positioning signal sent from transmitter 131. Similarly, respective transmitters 131 are installed on the ceilings of the second and third floors of medical institution 130. Here, time of each of transmitters 131 (hereinafter, referred to as "ground time") and times of GPS satellites 160-1, 160-3, 160-4, 160-2 (hereinafter, referred to as "satellite times") may be independent from one another, and need not be in synchronization. Preferably, the satellite times are in synchronization with one another.

The spread spectrum signal emitted as a positioning signal from each transmitter is generated by modulating a navigation message with a PRN (Pseudo Random Noise) code. The navigation message includes time data, orbit information, almanac, ionosphere correction data and the like. Further, each of transmitters 311 has data (for example, PRN-ID (Identification)) for identifying transmitter 311 itself or for identifying each of the GPS satellites on which transmitters 311 are mounted.

Mobile communication terminal 100 has data for generating each pseudo random noise code and a code generator. When receiving a positioning signal, mobile communication terminal 100 executes a demodulation process, which will be described later, using a code pattern of a pseudo random noise code allotted to each satellite, whereby it can specify a satellite having emitted the received signal. Moreover, in the new GPS signal, PRN-ID is included in the data, thereby preventing acquisition and tracking of the signal with an erroneous code pattern, which it is likely to be caused when the reception level is low.

The overview of the configuration of the transmitter mounted on the GPS satellite is as follows. Each of transmitters 311, 312, 313, 314 includes an atomic clock, a storage device for storing data, an oscillation circuit, a processing circuit for generating the positioning signal, an encoding circuit for spread-spectrum coding of the signal generated by the processing circuit, a transmission antenna, and the like. The storage device stores a navigation message and PRN-ID. The navigation message has ephemeris, almanac of each satellite, ionosphere correction data, and the like. The processing circuit generates a message for transmission, using time information from the atomic clock and various data stored in the storage device.

The code pattern of the pseudo random noise code for spread-spectrum coding is defined beforehand in each of transmitters 311, 312, 313, 314. Each code pattern differs transmitter by transmitter (that is, GPS satellite by GPS satellite). The encoding circuit performs spectrum-spreading of the message using such a pseudo random noise code. Each of transmitters 311, 312, 313, 314 converts the thus encoded signal to high frequency, and emits the resulting signal to the space through the transmission antenna.

As described above, each of transmitters 311, 312, 313, 314 emits a spread spectrum signal not causing harmful interference with other transmitters. Here, the "harmful interference" can be securely avoided by the output level so restrained as to prevent any interference. Alternatively, no harmful interference can be also realized by a manner of separating spectrum. The signal is transmitted using, for example, a carrier wave referred to as L1 band. Transmitters 311, 312, 313, 314 emit positioning signals having the same frequency, for example, in accordance with a spread spectrum communication method. Therefore, even when positioning signals transmitted from respective satellites are received by mobile communication terminal 100, the respective positioning signals can be received without cross-talk. As with the signals transmitted from the satellites, positioning signals from the plurality of transmitters on the ground can be received without cross-talk.

[IMES Transmitter]

Figure 4:
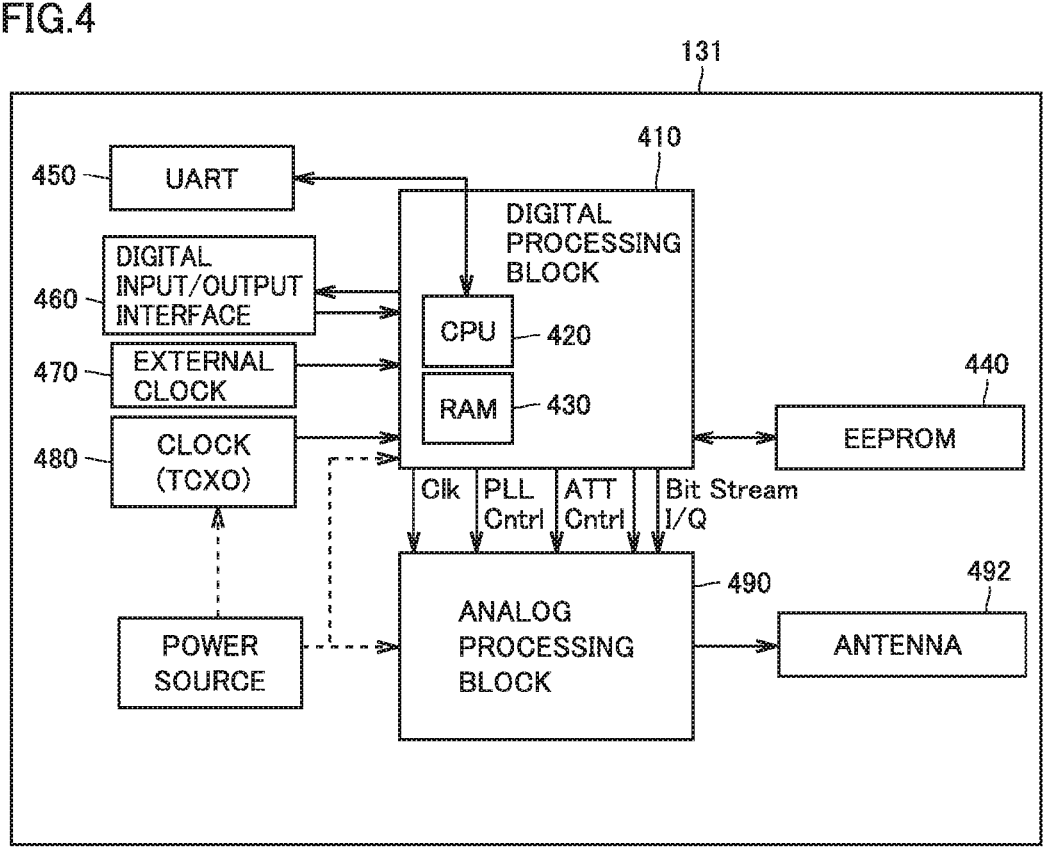
FIG. 4 is a block diagram showing a hardware configuration of a transmitter 131.

With reference to FIG. 4, transmitter 131 will be described. FIG. 4 is a block diagram showing the hardware configuration of transmitter 131. As shown in FIG. 4, transmitter 131 includes: a digital processing block 410; an EEPROM (Electronically Erasable and Programmable Read Only Memory) 440 electrically connected to digital processing block 410; a UART (Universal Asynchronous Receiver Transmitter) 450 electrically connected to digital processing block 410; a digital input/output interface 460 electrically connected to digital processing block 410; a clock 480 electrically connected to digital processing block 410; an analog processing block 490 electrically connected to digital processing block 410; an antenna 492 electrically connected to analog processing block 490; and a power source 494. Digital processing block 410 includes a CPU (Central Processing Unit) 420 and a RAM (Random Access Memory) 430.

EEPROM 440 stores: a program executed by CPU 420; data indicating the location in which transmitter 131 is installed; and the like. The program or data is read from EEPROM 440 when transmitter 131 is started, and is transferred to RAM 430. Further, EEPROM 440 can store data input from outside of transmitter 131. It should be noted that the storage device for storing the program or data is not limited to EEPROM 440. A storage device at least capable of storing data in a non-volatile manner may be used. As will be described later, when data is received from the outside, any storage device that allows data writing may be used. The data structure of EEPROM 440 will be described later.

Digital processing block 410 generates data, which serves as a source of signals transmitted by transmitter 131 as signals for positioning. Digital processing block 410 sends the generated data as a bit stream, to analog processing block 490. Clock 480 supplies a clock signal for defining the operation of CPU 420, or a clock signal for generating carrier wave, to digital processing block 410.

Digital input/output interface 460 can monitor an internal state (for example, "PLL Cntrl" signal) of the transmitter. Alternatively, digital input/output interface 460 can receive, from outside, (i) input of the code pattern of the pseudo random noise for spread modulation of the signal sent from transmitter 131 or (ii) input of data that defines transmission output. Furthermore, the input of other data to be sent from transmitter 131 can be also received. An example of the other data is text data representing a location where transmitter 131 is installed.

When input to transmitter 131, the code pattern of the pseudo spread code is written in a predefined area of EEPROM 440. Thereafter, the written PRN-ID is included in the signal for positioning. Other data are also written to areas ensured in advance in accordance with the data type, in EEPROM 440.

UART 450 converts data in the serial transfer format to/from data in parallel transfer format. An external clock 270 is used to adjust an operation of transmitter 131. For example, external clock 270 is used to receive input of frequency from a power line (not shown), and to calibrate the transmission frequency of the signal for positioning.

Analog processing block 490 performs modulation to carrier wave of 1.57542 GHz using a bit stream output from digital processing block 410 to generate a transmission signal, and outputs it to antenna 492. The signal is sent from antenna 492. In this way, the signal having the same configuration as that of the signal for positioning is sent from transmitter 131. In this case, the content of the signal is not completely the same as the content included in the positioning signal sent from the satellite. An example of the configuration of signal emitted from transmitter 131 will be described later.

Power source 494 supplies power to each component included in transmitter 131. It should be noted that as shown in FIG. 4, power source 494 may be provided inside transmitter 131, or external power supply may be received.

In the description above, CPU 420 is used as a calculation processing device for implementing the process in digital processing block 410, but other calculation processing devices may be used. Moreover, since the operation implemented by transmitter 131 is not complicated, digital processing block 410 can be implemented by an electric circuit configured to implement each process instead of CPU 420, for example. Further, though a clock signal (Clk) is supplied from digital processing block 410 to analog processing block 490 in FIG. 4, it may be directly supplied from clock 480 to analog processing block 490. For clearer description, in the present embodiment, digital processing block 410 and analog processing block 490 are shown separately. Physically, these blocks may be mounted together on one chip.

[Data Structure]

Figure 5:
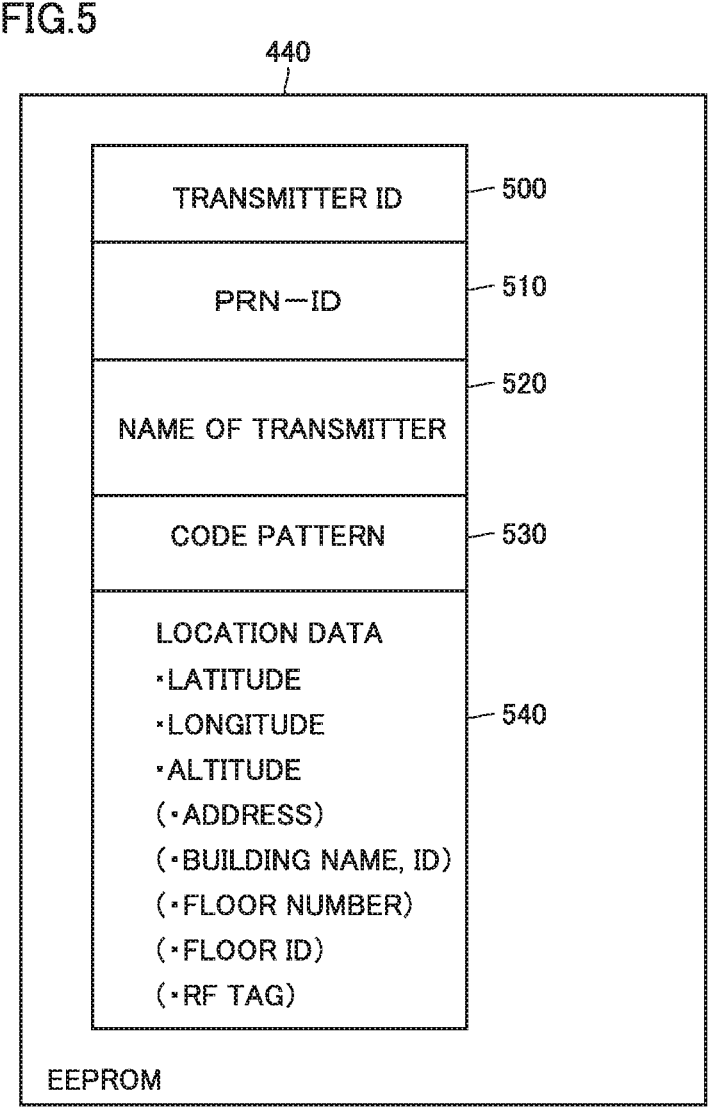
FIG. 5 schematically shows a manner of data storage in an EEPROM 440 provided in transmitter 131.

With reference to FIG. 5, the following describes the data structure of transmitter 131. FIG. 5 schematically shows a manner of data storage in EEPROM 440 provided in transmitter 131. EEPROM 440 includes areas 500 to 540 for storing data. Area 500 stores a transmitter ID, as a number for identifying the transmitter. The transmitter ID is, for example, numerals and/or alphabets or other combination written in a non-volatile manner in the memory, when the transmitter is manufactured. The PRN-ID of the pseudo spread code allotted to the transmitter is stored in area 510. The name of the transmitter is stored as text data in area 520.

The code pattern of the pseudo spread code allotted to the transmitter is stored in area 530. The code pattern of the pseudo spread code is selected from a plurality of finite number of code patterns allotted beforehand to the location information providing system according to the embodiment of the present invention. The code pattern thereof is different from the code pattern of the pseudo spread code allotted to each satellite. Moreover, as described above, the code pattern of the pseudo spread code can be changed to other code patterns input via digital input/output interface 460.

Although the code patterns of the pseudo spread code allotted to the present location information providing system are finite in number, the number of transmitters differs depending on the size of the installation location for each transmitter or the configuration of the installation location (floor number in a building). A plurality of transmitters more than the number of the code patterns may be used. Therefore, there may be a plurality of transmitters having the same code pattern of the pseudo spread code. In that case, the installation locations of the transmitters having the same code pattern may be determined in consideration of signal output. This prevents simultaneous reception of a plurality of positioning signals using the same code pattern of the pseudo spread code by the same mobile communication terminal.

Location data for specifying the location where transmitter 131 is installed is stored in area 540. The location data is represented, by way of example, as a combination of latitude, longitude, and altitude. In area 540, in addition to or instead of the location data, the address, the name or building ID of a building, the floor number, the floor ID, an RF tag, and the like may be stored.

[Configuration of Mobile Communication Terminal]

Figure 6:
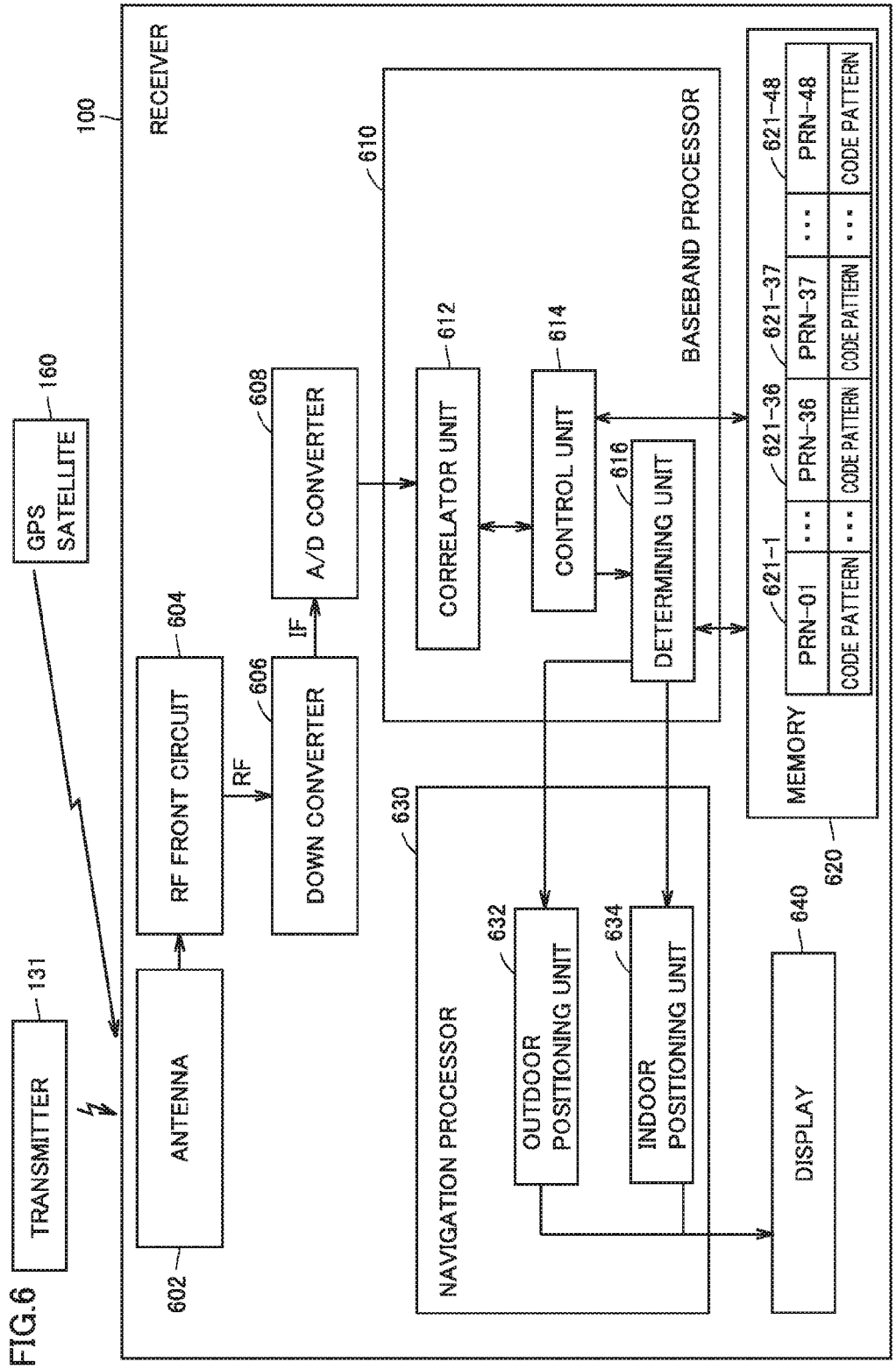
FIG. 6 is a block diagram showing one configuration of a positioning function of a mobile communication terminal 100.

With reference to FIG. 6, the following describes a configuration of mobile communication terminal 100. FIG. 6 is a block diagram showing one configuration of the positioning function of mobile communication terminal 100. Mobile communication terminal 100 includes: an antenna 602; a RF (Radio Frequency) front circuit 604 electrically connected to antenna 602; a down converter 606 electrically connected to RF front circuit 604; an A/D (Analog to Digital) converter 608 electrically connected to down converter 606; a baseband processor 610 electrically connected to A/D converter 608; a memory 620 electrically connected to baseband processor 610; a navigation processor 630 electrically connected to baseband processor 610; and a display 640 electrically connected to navigation processor 630.

Memory 620 includes a plurality of areas for storing code patterns of pseudo random noise codes, which are data for identifying the emission sources of the positioning signals. By way of example, according to an aspect, when 48 code patterns are used, memory 620 includes areas 621-1 to 621-48 as shown in FIG. 6. According to another aspect, when a larger number of code patterns are used, a larger number of areas are secured in memory 620. On the contrary, it is also possible that code patterns smaller in number than the areas secured in memory 620 are used.

Consider an example in which 48 code patterns are used. Here, if 24 satellites are used for the satellite positioning system, 24 identification data for identifying the respective satellites and 12 spare data are stored in areas 621-1 to 621-36. Here, in area 621-1, for example, a code pattern of a pseudo noise code for the first satellite is stored. By reading the code pattern therefrom and performing cross-correlation process with the received signal, signal tracking and deciphering of navigation message included in the signal become possible. Though a method in which the code pattern is stored and read has been described as an example here, a method is also possible in which the code pattern is generated by a code pattern generator. The code pattern generator is realized, for example, by combining two feedback shift registers. Configuration and operation of the code pattern generator are readily understood by a person skilled in the art. Therefore, detailed description thereof will not be repeated here.

Similarly, code patterns of pseudo noise codes allotted to the transmitters for emitting positioning signals are stored in areas 621-37 to 621-48. For example, a code pattern of a pseudo noise code allotted to the first transmitter is stored in area 621-37. In this case, in the present embodiment, transmitters having 12 code patterns are usable; however, transmitters may be arranged such that transmitters having the same code pattern are not placed in a scope of coverage of the same mobile communication terminal. By such an arrangement, 12 or more transmitters can be installed on the same floor of medical institution 130, for example.

Baseband processor 610 includes: a correlator unit 612 that accepts input of a signal output from A/D converter 608; a control unit 614 that controls an operation of correlator unit 612; and a determining unit 616 that determines from where a positioning signal is sent, based on the data output from control unit 614. Navigation processor 630 includes: an outdoor positioning unit 632 for measuring the location of mobile communication terminal 100 in the outdoor based on the signal output from determining unit 616; and an indoor positioning unit 634 for deriving information indicating the location of mobile communication terminal 100 in indoor, based on the data output from determining unit 616.

Antenna 602 can receive positioning signals emitted from GPS satellites 160-1, 160-3, 160-4, respectively, and a positioning signal emitted from transmitter 131. Further, when mobile communication terminal 100 is implemented as a mobile phone, antenna 602 can transmit/receive a signal for wireless telephone or a signal for data communication, in addition to the signals mentioned above.

RF front circuit 604 receives the signal received by antenna 602, and performs a filtering process or the like to remove noise or only output a signal having a predefined bandwidth. The signal output from RF front circuit 604 is input to down converter 606. Down converter 606 amplifies the signal output from RF front circuit 604, and outputs it as an intermediate frequency signal. The signal is input to A/D converter 608. A/D converter 608 performs digital conversion of the input intermediate frequency signal, to digital data. The digital data is input to baseband processor 610.

In baseband processor 610, correlator unit 612 performs a correlation process between (i) the code pattern read from memory 620 by control unit 614 and (ii) the received signal. For example, correlator unit 612 performs matching between (i) two types of code patterns different by 1 bit in code phase as provided by control unit 614 and (ii) the digital data sent from A/D converter 608. Correlator unit 612 uses each code pattern to track a positioning signal received by mobile communication terminal 100, and specify a code pattern having an array coinciding with the bit array of the positioning signal. Consequently, the code pattern of the pseudo noise code is specified and, therefore, mobile communication terminal 100 can determine from which satellite or from which transmitter the received positioning signal has been transmitted. Further, mobile communication terminal 100 can demodulate and decipher a message using the specified code pattern.

More specifically, determining unit 616 makes such determination as described above, and transmits data in accordance with the result of determination to navigation processor 630. Determining unit 616 determines whether or not the PRN-ID included in the received positioning signal is the PRN-ID allotted to the transmitter other than a transmitter mounted on a GPS satellite.

Here, an example will be described in which 24 GPS satellites are used in the positioning system. Here, 36 pseudo noise codes, including spare codes, are used, for example. In this case, PRN-01 to PRN-24 are used as numbers (PRN-IDs) for identifying respective GPS satellites, and PRN-25 to PRN-36 are used as numbers for identifying spare satellites. The spare satellite refers to a satellite launched in addition to the originally launched satellites. Specifically, such a satellite is launched in order to prepare for failure of a GPS satellite or a transmitter or the like mounted on a GPS satellite.

Further, it is assumed that code patterns of 12 pseudo noise codes are allotted to a transmitter (transmitter 131 or the like) other than the transmitters mounted on the GPS satellites. Here, numbers different from the PRN-IDs allotted to the satellites, for example, PRN-37 to PRN-48, are allotted to the respective transmitters. Therefore, in the this example, there are 48 PRN-IDs. Here, PRN-ID to PRN-48 are allotted to the transmitters in accordance with, for example, the arrangement of transmitters. Therefore, if used transmission output is not such that it causes interference of signals emitted from the transmitters, the same PRN-ID may be used for different transmitters. This arrangement allows use of transmitters larger in number than the PRN-IDs allotted for the transmitters on the ground.

Therefore, determining unit 616 makes reference to code patterns 422 of the pseudo noise codes stored in memory 620 to determine whether the code pattern obtained from the received positioning signal matches a code pattern allotted to an transmitter. If these code patterns match, determining unit 616 determines that the positioning signal has been emitted from a transmitter. Otherwise, determining unit 616 determines that the signal has been emitted from a GPS satellite, and determines, with reference to the code patterns stored in memory 620, to which GPS satellite the obtained code pattern has been allotted. Though it has been illustrated that the code pattern is used for determination, the determination may be made by comparison of other data. For example, comparison using PRN-IDs may be used for the determination.

If the received signal is emitted from a GPS satellite, determining unit 616 transmits the data obtained from the specified signal to outdoor positioning unit 632. The data obtained from the signal includes a navigation message. If the received signal is emitted from transmitter 131 or the like, determining unit 616 transmits data obtained from the signal to indoor positioning unit 634. The data represents coordinate values set in advance, as data for specifying the location of transmitter 131. According to another aspect, a number for identifying the transmitter may be used.

In navigation processor 630, outdoor positioning unit 632 executes a process for calculating the location of mobile communication terminal 100 based on the data transmitted from determining unit 616. More specifically, using data included in signals emitted from three or more (preferably, four or more) GPS satellites, outdoor positioning unit 632 calculates propagation time of each signal, and based on the result of calculation, finds the location of mobile communication terminal 100. The process is executed by a known method of satellite positioning. The process can be readily understood by a person skilled in the art. Therefore, detailed description thereof will not be repeated.

On the other hand, in navigation processor 630, indoor positioning unit 634 performs a positioning process for a case where mobile communication terminal 100 is present in indoor, based on the data output from determining unit 616. As described below, transmitter 131 emits a positioning signal including data (time data) for specifying a location. Therefore, if mobile communication terminal 100 receives such a signal, data can be extracted from the signal and can be used to find the location of mobile communication terminal 100. Indoor positioning unit 634 performs this process. Data calculated by outdoor positioning unit 632 or indoor positioning unit 634 is used for presentation on display 640. Specifically, these data are incorporated in data for displaying a screen, and an image representing the measured location or an image for displaying the location where transmitter 131 is installed is generated and displayed on display 640.

Figure 7:
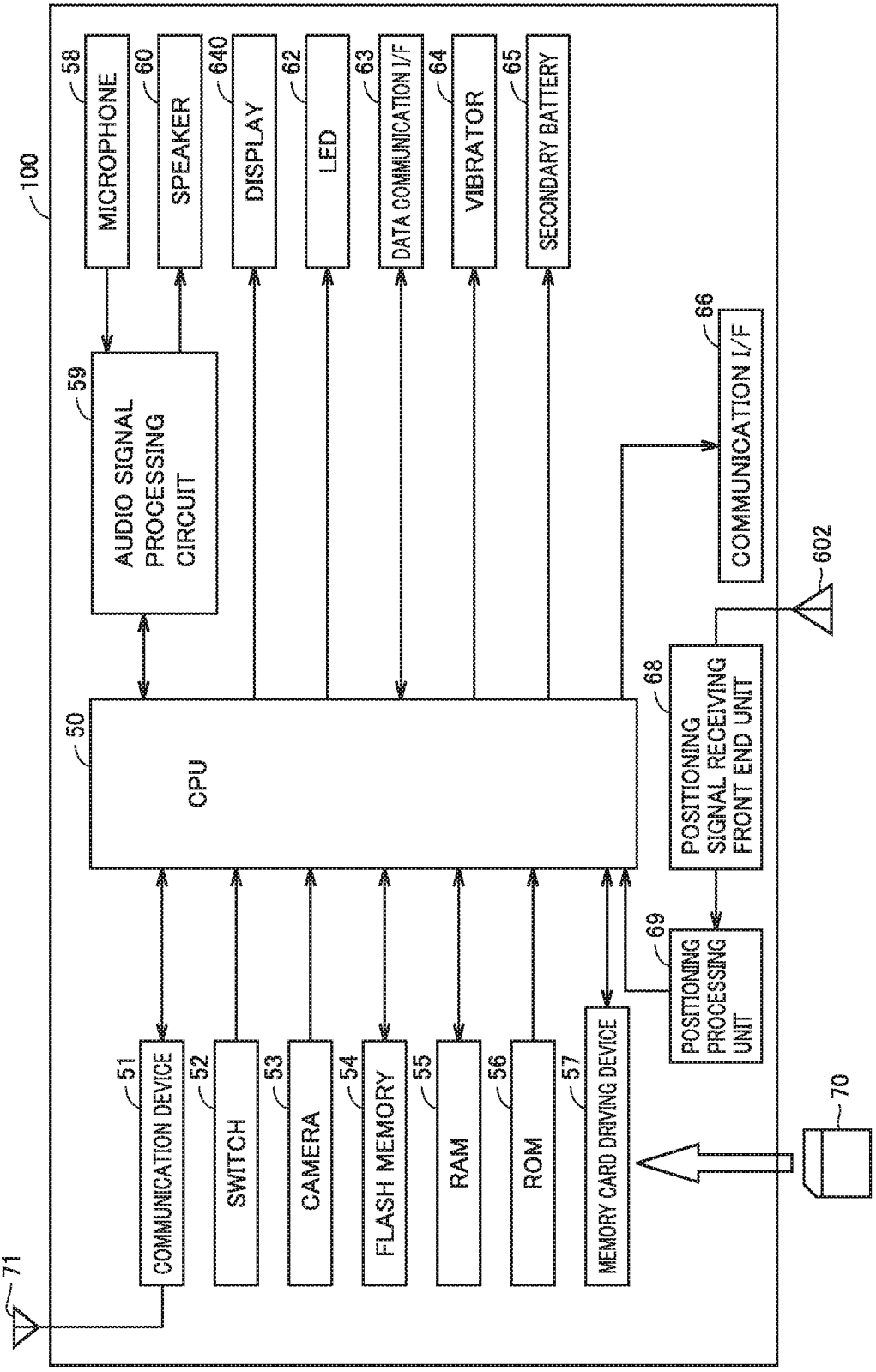
FIG. 7 is a block diagram showing a hardware configuration of mobile communication terminal 100 according to the embodiment of the present invention.

With reference to FIG. 7, the following describes a configuration of mobile communication terminal 100 according to the present embodiment. FIG. 7 is a block diagram showing a hardware configuration of mobile communication terminal 100 according to the embodiment of the present invention. Mobile communication terminal 100 includes a CPU 50, a communication device 51, a switch 52, a camera 53, a flash memory 54, a RAM 55, a ROM 56, a memory card driving device 57, a microphone 58, an audio signal processing circuit 59, a speaker 60, a display 640, an LED (Light Emitting Diode) 62, a data communication I/F (Interface) 63, a vibrator 64, a secondary battery 65, a communication I/F 66, a GPS antenna 602, a positioning signal receiving front end unit 68, and a positioning processing unit 69. To memory card driving device 57, memory card 70 can be attached.

Antenna 71 receives a signal sent by a base station, or transmits a signal for communicating with other communication devices via the base station. The signal received by antenna 71 is subjected to a front end process performed by communication device 51, and then the signal thus processed is sent to CPU 50.

Switch 52 is implemented by a touch panel or a hard switch, and receives input of a command for mobile communication terminal 100. CPU 50 performs a process for controlling an operation of mobile communication terminal 100 based on the command provided to mobile communication terminal 100. When mobile communication terminal 100 receives the signal, CPU 50 performs a predefined process based on the signal sent from communication device 51, and sends the processed signal to audio signal processing circuit 59. Audio signal processing circuit 59 performs a predefined signal process to the signal, and sends the processed signal to speaker 60. Speaker 60 outputs a sound based on the signal.

Microphone 58 accepts speech to mobile communication terminal 100, and sends, to audio signal processing circuit 59, a signal corresponding to the speech thus made. Based on the signal, audio signal processing circuit 59 performs a predefined process for phone call, and sends the processed signal to CPU 50. CPU 50 converts the signal into data for transmission, and sends the converted data to communication device 51. Communication device 51 generates the signal for transmission using the data, and sends the signal to antenna 71.

Flash memory 54 stores data sent from CPU 50. Moreover, CPU 50 reads data stored in flash memory 54, and performs a predefined process using the data. RAM 55 holds temporarily data generated by CPU 50 based on an operation performed to switch 52. ROM 56 stores a program or data for causing mobile communication terminal 100 to perform a predetermined operation. CPU 50 reads the program or data from ROM 56, and controls an operation of mobile communication terminal 100.

Memory card driving device 57 reads data stored in memory card 70, and sends it to CPU 50. Memory card driving device 57 writes data, output by CPU 50, in an empty area of memory card 70.

Audio signal processing circuit 59 performs the signal process for phone call as described above. It should be noted that in the example shown in FIG. 7, CPU 50 and audio signal processing circuit 59 are illustrated as separate configurations; however, in another aspect, CPU 50 and audio signal processing circuit 59 may be configured in one piece.

Although display 350 is a touch panel type display, but the structure of the touch panel is not particularly limited. Based on data obtained from CPU 50, display 350 displays an image defined by the data. For example, display 350 displays a still image, a motion image, and the attribute of a music file (the name of the file, a player, performance time, and the like) stored in flash memory 54.

Based on the signal from CPU 50, LED 62 implements a predetermined light emission operation. Data communication I/F 63 accepts attachment of a cable for data communication. Data communication I/F 63 sends, to the cable, the signal output from CPU 50. Alternatively, data communication I/F 63 sends, to CPU 50, the data received via the cable. Communication I/F 66 employs the NFC communication function to communicate with other devices each having the NFC communication function. Vibrator 64 vibrates at a predetermined frequency based on a signal output from CPU 50.

GPS antenna 602 receives a signal sent from a GPS satellite, and sends the received signal to positioning signal receiving front end unit 68. Positioning signal receiving front end unit 68 performs pattern matching based on each of signals received from at least three (desirably four or more) GSP satellites. When the code pattern included in each signal matches with the code pattern held by mobile communication terminal 100, positioning signal receiving front end unit 68 sends the signal to positioning processing unit 69. Positioning processing unit 69 performs the positioning process using the signal, and calculates the location of mobile communication terminal 100 having received the signal. CPU 50 displays the result of calculation on display 350.

In a certain aspect, secondary battery 65 may include a plurality of battery packs. In this case, a main battery pack of a plurality of battery modules is attachable/detachable, and a sub battery pack may be a built-in type battery pack. In this way, even if the main battery pack is detached for replacement, mobile communication terminal 100 can be driven by power supplied from the sub battery pack.

[Configuration of Computer]

Figure 8:
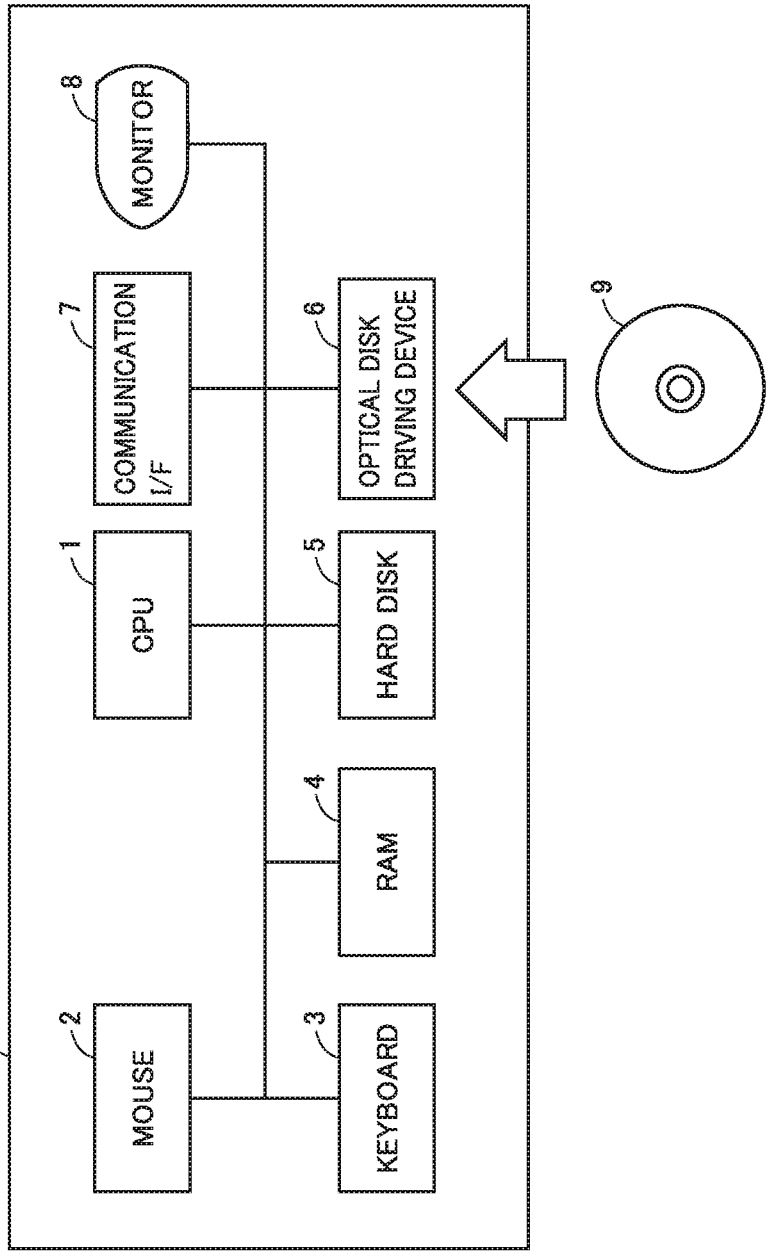
FIG. 8 is a block diagram showing a configuration of a computer 800 having a well-known configuration.

With reference to FIG. 8, the following describes a configuration of computer 800 for implementing regional medical data bank system 120 or terminal device 133 according to the present embodiment. FIG. 8 is a block diagram showing the configuration of computer 800 having a well-known configuration. In the present embodiment, each of location information management server 110, server 120A, server 120B, terminal device 133, utilization terminal 141, information processing device 1910, space-time ID management system 1930, information processing terminal 1940, and the like is implemented using the configuration such as computer 800.

More specifically, as main components, computer 800 includes: a CPU 1 for executing a program; a mouse 2 and a keyboard 3 each for receiving input of instruction provided by a user of computer 800; a RAM 4 for storing, in a volatile manner, data generated by CPU 1 executing a program or data input via mouse 2 or keyboard 3; a hard disk 5 for storing data in a non-volatile manner; an optical disk driving device 6; a communication I/F 7; and a monitor 8. The components are connected to one another via a bus. To optical disk driving device 6, a CD-ROM 9 or another optical disk is attached. Communication I/F 7 includes a USB (Universal Serial Bus) interface, a wired LAN (Local Area Network), a wireless LAN, a Bluetooth® interface, and the like, but is not limited to these.

The process in computer 800 is implemented by hardware constituting computer 800 and software executed by CPU 1. Such software may be stored in hard disk 5 in advance. Moreover, the software may be distributed as a program product with the software being stored in a CD-ROM 9 or another computer-readable non-volatile data recording medium. Alternatively, the software may be provided, as a downloadable program product, by an information provider connected to the Internet or other networks. Such software is read from the data recording medium by optical disk driving device 6 or other data reading devices or is downloaded via communication I/F 7, and is then temporarily stored in hard disk 5. The software is read from hard disk 5 by CPU 1, and is stored in RAM 4 in the form of an executable program. CPU 1 executes the program.

Each of the components included in computer 800 shown in FIG. 8 is a general component. Hence, it can be said that the most essential part in the present embodiment is the program stored in computer 800. The operation of the hardware of computer 800 is well known and is therefore not repeatedly described in detail.

It should be noted that the data recording medium is not limited to a CD-ROM, a FD (Flexible Disk), and a hard disk, and may be a nonvolatile data recording medium that carries a program in a fixed manner. Examples of such a nonvolatile data recording medium include a magnetic tape, a cassette tape, an optical disk (MO (Magnetic Optical Disk)/MD (Mini Disk)/DVD (Digital Versatile Disk)), an IC (Integrated Circuit) card (inclusive of a memory card), an optical card, and a semiconductor memory such as a mask ROM, an EPROM (Electronically Programmable Read-Only Memory), an EEPROM, or a flash ROM. The term "program" herein can include not only a program directly executable by a CPU, but also a program in a source program format, a compressed program, an encrypted program, and the like.

[Space-Time ID]

Figure 9:
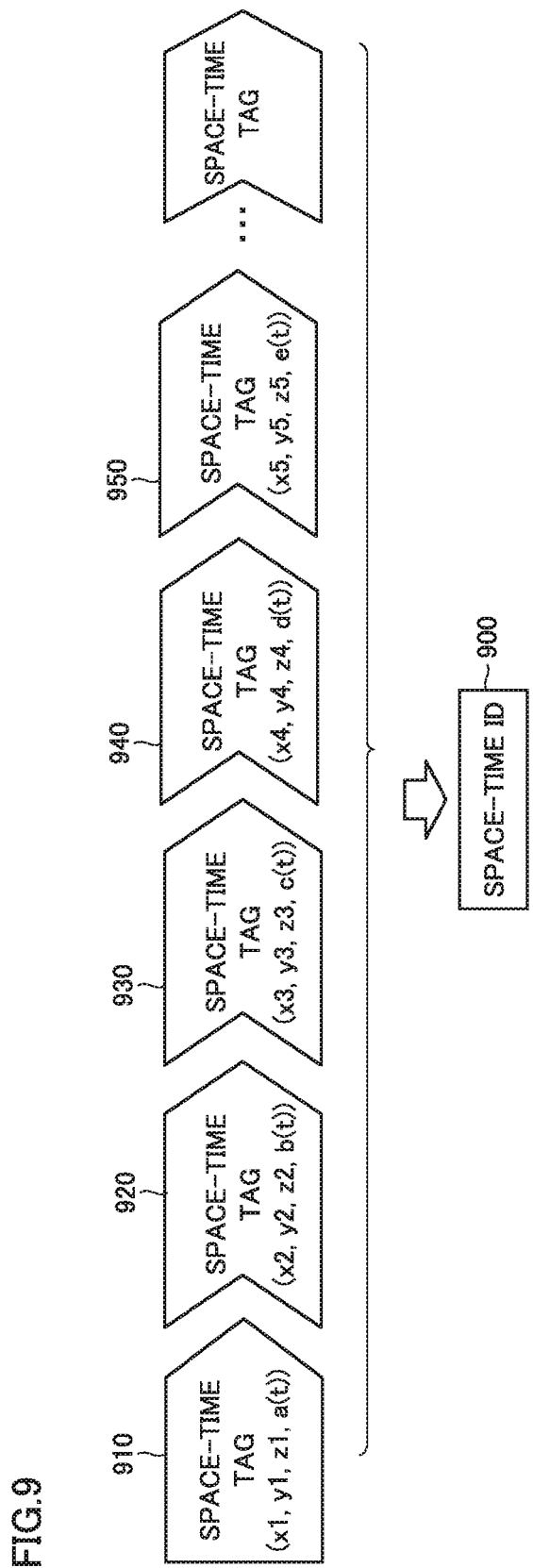
FIG. 9 shows a detail of a space-time ID according to the embodiment of the present invention.

With reference to FIG. 9, the following describes the space-time ID according to the present embodiment. FIG. 9 shows details of the space-time ID according to the embodiment of the present invention. In a certain aspect, space-time ID 900 includes space-time tags 910, 920, 930, 940, 950 and the like. Each space-time tag includes location information and time information as information elements. The location information includes data for indicating coordinate values of a space, such as latitude x, longitude y, and altitude z. The location information is not limited to location information specified based on a signal sent from a GPS or different positioning satellite. For example, the location information may also include information specified based on a signal sent by transmitter 131. This information is not limited to the latitude, longitude, and altitude, and may be indicated by the floor number of a building, a floor ID, a RF tag, and the like. For example, the time information may include one of (i) time data obtained from a positioning signal transmitted by GPS satellite 160 and (ii) time data included in a signal sent by transmitter 131. The space-time tag is associated with biological information, medical diagnosis information, medication information, and other living information of the patient. The space-time tag is generated at every certain time (such as every 30 seconds), for example. Alternatively, in another aspect, the space-time tag may be generated in response to an operation of the user of mobile communication terminal 100. In another aspect, the space-time tag may be generated in response to a generation instruction sent from the provider of service joined by the user of mobile communication terminal 100.

In the present embodiment, the location and time of mobile communication terminal 100 are continuously acquired, thereby obtaining unique information of an individual person (ID of a specific individual person). As shown in the series of space-time tags 910, 920, 930, 940, 950, the space-time ID, which is a chunk of continuous information elements without interruption, represents activities of the individual person. Therefore, the space-time ID, which is a collection of space-time tags, is used for identification of the information of the individual person.

First, the location of mobile communication terminal 100 is specified by three-dimensional information (for example, latitude x, longitude y, altitude z), floor ID, RF tag and other information as described above. On this occasion, if mobile communication terminal 100 is in the outdoor and can receive positioning signals sent from at least four GPS satellites 160, mobile communication terminal 100 obtains location information based on the at least four positioning signals. When mobile communication terminal 100 is in the indoor as in medical institution 130, mobile communication terminal 100 cannot receive a positioning signal transmitted by GPS 160. In this case, mobile communication terminal 100 specifies the location information based on a pseudo signal transmitted by transmitter 131 or another transmitter.

Furthermore, by adding time information (t) to the obtained location information, the location of mobile communication terminal 100 is specified in four dimensions. In this case, precision of the time information is maintained using, for example, a UTC (Coordinated Universal Time) based time stamp server.

In the example shown in FIG. 9, combinations of times a(t), b(t), c(t), d(t), and e(t) with respective pieces of location information at these times are defined as space-time tags 910, 920, 930, 940, 950.

It should be noted that the location information is not always the same. For example, the land of Japan is located at a plurality of plate boundaries, and these plates move in different directions to result in a complicated crustal movement. Accordingly, a reference point used for location survey is also affected by the crustal movement, with the result that an actual location on the earth and its coordinate values indicated by the location survey result will differ from each other over time. For example, although it depends on a location, it is said that the surface of the earth moves by about 6 cm in one year. Hence, in order to maintain precision of location information (latitude, longitude, and altitude) for a long time, influence of strain provided by the crustal movement can be corrected. Hence, map information used in the present embodiment is also desirably updated regularly.

Moreover, in view of such a crustal movement, location information stored in space-time ID information DB 122 will not possibly correspond to an actual location in several tens years. Therefore, for such a case, for the purpose of correction of the location information, version information of the map information upon the obtainment of the location information may be stored in space-time ID information DB 122. By using the map information specified by the version information, the location information stored in space-time ID information DB 122 can be corrected. It should be noted that the crustal movement affecting the location information and the correction thereof are well known for one having ordinary skill in the art. Hence, they are not described more in detail.

[Relation Between Location Information and Time Information]

Figure 10:
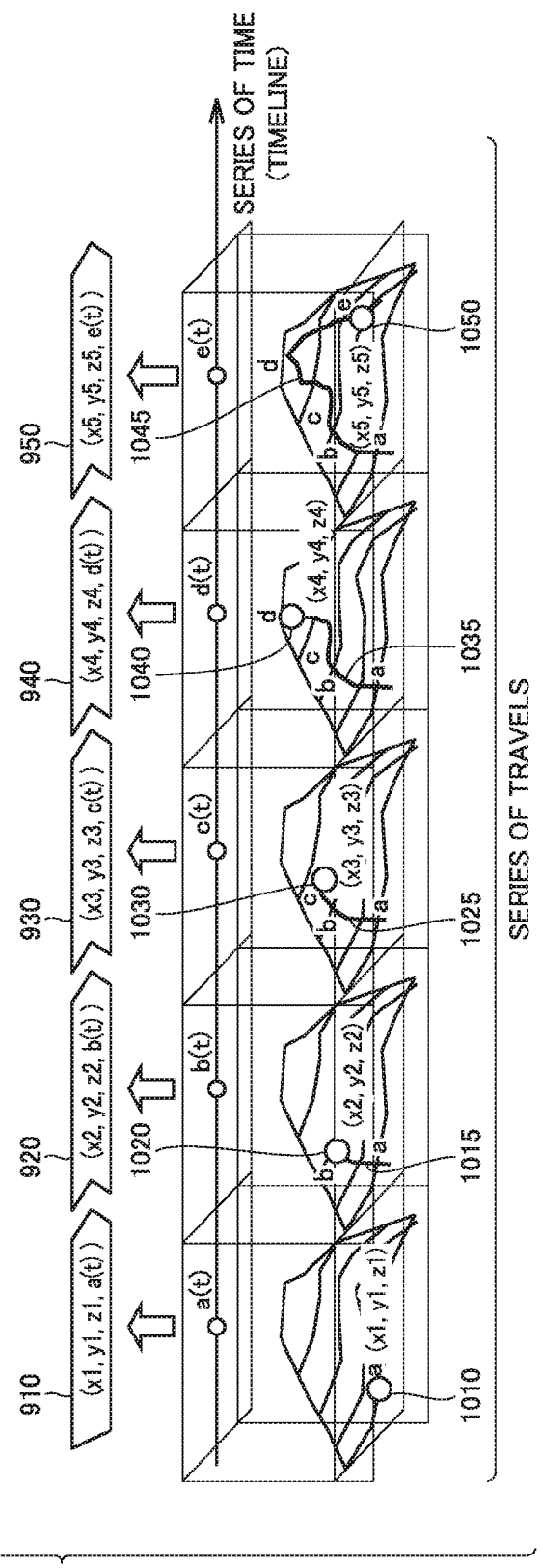
FIG. 10 conceptually shows a continuous relation between location information and time information in the embodiment of the present invention.

With reference to FIG. 10, the following further describes the continuous information elements. FIG. 10 conceptually shows a continuous relation between the location information included in the information element and the time information in the present embodiment. In the present embodiment, location information 1000 is indicated by the latitude, longitude, altitude, and time information, for example. Further, by continuously obtaining location information of an individual person, a track of activities of the individual person can be understood. The location information of the individual person constitutes a space-time tag. A plurality of such space-time tags constitute a space-time ID.

In a certain aspect, at time a(t), the user of mobile communication terminal 100 is present in a place 1010, for example. On this occasion, space-time tag 910 of the user includes time information (time a(t)) and location information (latitude x1, longitude y1, and altitude z1 in place 1010) at time a(t).

Then, at time b(t), the user of mobile communication terminal 100 is present in a place 1020. On this occasion, space-time tag 920 of the user includes time information (time b(t)) and location information (latitude x2, longitude y2, and altitude z2 in place 1020) at time b(t). Moreover, a traveling path of the user from place 1010 to place 1020 is represented by a track 1015. Track 1015 corresponds to space-time ID from time a(t) to time b(t). Precision of track 1015 is dependent on how frequently the positioning is performed during a period of time a(t) to time b(t). The positioning is performed at the following timing: at a predetermined time interval; when a predetermined acceleration is detected; when mobile communication terminal 100 receives another signal from medical institution 130 or another institution; or the like. The positioning may be performed at other timings. The same applies to the description below.

Then, at time c(t), the user is present in a place 1030. On this occasion, space-time tag 930 of the user includes time information (time c(t)) and the location information (latitude x3, longitude y3, altitude z3 in place 1030) at time c(t). A traveling path of the user from places 1010 to 1030 is represented by a track 1025. Track 1025 corresponds to the space-time ID from time a(t) to time c(t).

Then, at time d(t), the user is present in a place 1040. On this occasion, space-time tag 940 of the user includes time information (time d(t)) and location information (latitude x4, longitude y4, altitude z4 in place 1040) at time d(t). A traveling path of the user from place 1010 to place 1040 is represented by a track 1035. Track 1035 corresponds to the space-time ID from time a(t) to time d(t).

Then, at time e(t), the user is present in a place 1050. On this occasion, space-time tag 950 of the user includes time information (time e(t)) and location information (latitude x5, longitude y5, and altitude z5 in place 1050) at time e(t). A track from place 1010 to place 1050 is specified as a track 1045. Track 1015 corresponds to space-time ID from time a(t) to time d(t).

[Tagged Data Accumulated Using Space-Time ID]

Figure 11:
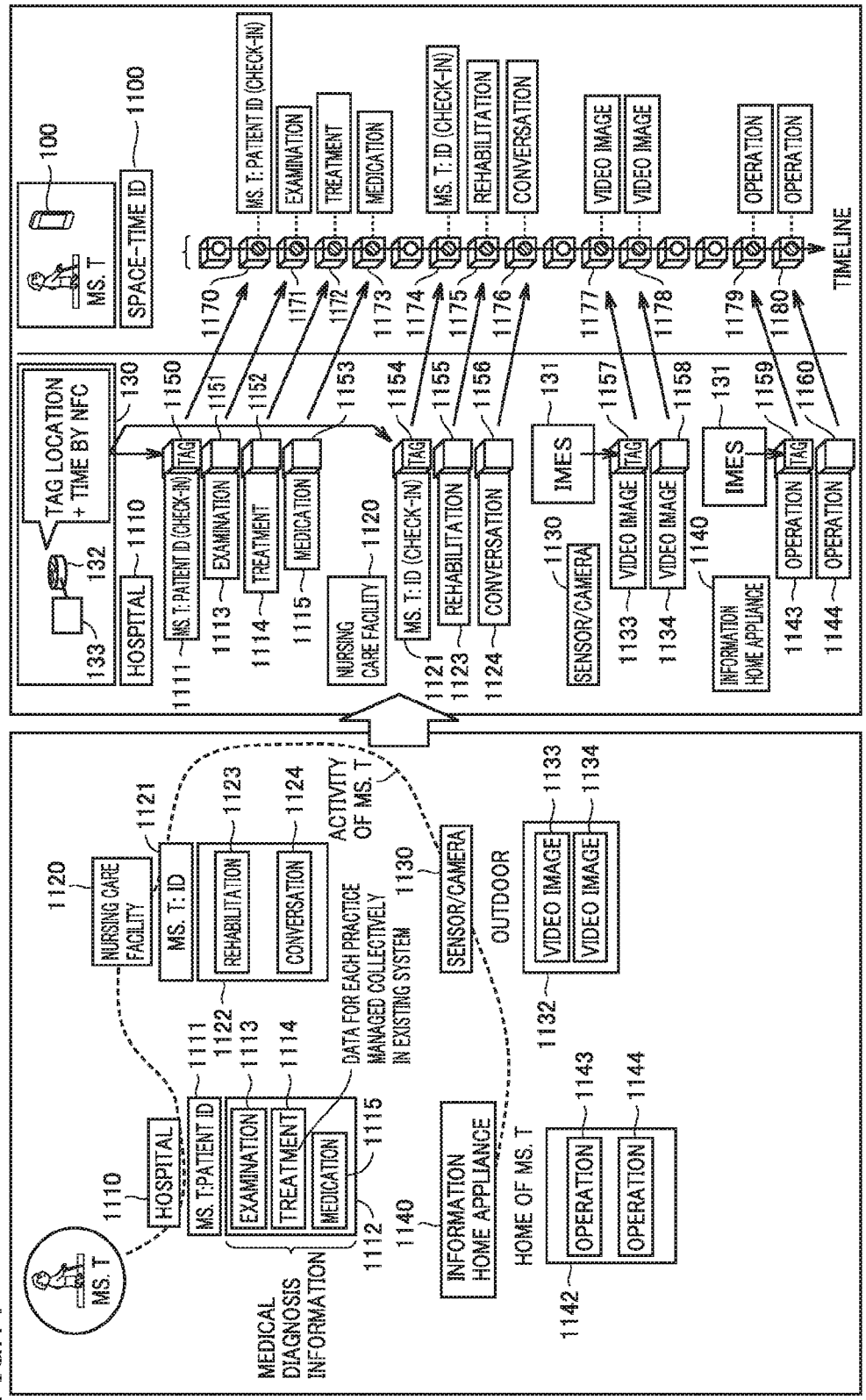
FIG. 11 shows a manner in which the data associated with each of services provided to a user of mobile communication terminal 100 is associated with the tag.

With reference to FIG. 11, data accumulated using the space-time tag will be described. FIG. 11 shows a manner in which the data associated with each of services provided to the user of mobile communication terminal 100 is associated with the "space-time tag".

In a certain aspect, a user (for example, Ms. T) goes to a hospital 1110. In hospital 1110, the user is subjected to medical diagnosis. On this occasion, the user is associated with a patient ID 1111. Further, medical diagnosis information 1112 includes examination data 1113, treatment data 1114, and medication data 1115. Mobile communication terminal 100, which serves as the PHR card, obtains location information at every constant time, and transmits the location information and the terminal information to regional medical data bank system 120.

Then, the user goes to a nursing care facility 1120. The user has a user ID 1121 assigned by a service provider to receive a service provided by nursing care facility 1120. Data 1122 indicating the service provided by nursing care facility 1120 includes rehabilitation data 1123 and conversation data 1124. For example, rehabilitation data 1123 include a type, content, or the like of the rehabilitation provided in nursing care facility 1120. For example, conversation data 1124 includes a type, time, content, or the like of conversation with a nursing care support person in nursing care facility 1120.

Then, the user comes out of nursing care facility 1120 and goes to her home. On the way to her home, the user walks outdoors where a sensor/camera 1130 is installed. On this occasion, sensor/camera 1130 detects the walking user, and obtains monitoring data 1132 as a monitoring result. Monitoring data 1132 includes video image data 1133, 1134. For example, video image data 1133 indicates a video image obtained when the user is first captured by sensor/camera 1130. Video image data 1134 indicates a video image obtained just before the user goes out of the field of view of sensor/camera 1130.

The user passes through the detection range of sensor/camera 1130 and heads toward her home. At the home of the user, an information home appliance 1140 is installed. Information home appliance 1140 is a self-traveling robot or another device, for example. The device includes, for example, a detection function to receive an operation from the user, and includes a camera to capture an image of the user. In response to the user's operation, information home appliance 1140 outputs information 1142. Information 1142 includes operation data 1143, 1144. Operation data 1143 is data obtained after the user switches on information home appliance 1140, for example. For example, operation data 1144 includes a type or content of a command provided to information home appliance 1140. For example, when information home appliance 1140 is a television, operation data 1143 includes a selected channel. Operation data 1143 is data obtained when the user turns off the switch of information home appliance 1140. When information home appliance 1140 is a television, operation data 1144 includes data indicating that the television is powered off.

In the above example, hospital 1110, nursing care facility 1120, sensor/camera 1130, and information home appliance 1140 may provide different users ID. Hence, in such a case, it is difficult to achieve commonality among individually assigned users ID. Moreover, for example, an ID currently under review by medical NDD or the like is an anonymous ID, with which an individual person cannot be specified. Hence, information assigned such an ID cannot be reused in other medical institutions.

Moreover, data formats created in hospital 1110, nursing care facility 1120, sensor/camera 1130, and information home appliance 1140 are generally different from one another. It is not easy to collect pieces of data different in format. Accordingly, a technique is required which enables reuse of data in other organizations and which facilitates collection of data.

In view of this, the use of space-time tag and space-time ID according to the present embodiment enables reuse of data and facilitates collection of data. Hereinafter, this point will be described in detail. In a certain aspect, NFC terminal 132 installed in medical institution 130 or another institution tags location information and time information.

More specifically, in hospital 1110, user ID 1111 is associated with a space-time tag 1150. Space-time tag 1150 includes: time information indicating the date and time at which the user has checked in at the reception of hospital 1110; and location information indicating the location at which the user has checked in. Examination data 1113 is associated with a space-time tag 1151. Space-time tag 1151 includes: time information indicating time at which examination has been performed; and location information for identifying a consultation room for the examination or a device used for the examination. Treatment data 1114 is associated with space-time tag 1152. Space-time tag 1152 includes: time information indicating time at which the treatment has been performed (for example, day, hour, and minute at which the electronic health record system receives an input indicating that the treatment has been completed); and location information indicating the location at which the treatment has been performed. Medication data 1115 is associated with a space-time tag 1153. Space-time tag 1153 includes: time information indicating time at which the medication has been provided; and location information indicating the location at which the medication has been provided. As described above, the location information can include: location information obtained using signals from GPS satellites 160; and location information received from a device for transmitting the location information, such as transmitter 131.

In another aspect, user ID 1121 is associated with a space-time tag 1154 in nursing care facility 1120. Space-time tag 1154 includes: time information indicating time at which the user has checked in at the reception of nursing care facility 1120 (for example, day, hour, minute, and second at which an input has been provided to the system to indicate that the user has checked in at the reception of nursing care facility 1120); and the location information indicating the location at which the user has checked in. Rehabilitation data 1123 is associated with a space-time tag 1155. Space-time tag 1155 includes: time information indicating time at which the rehabilitation has been performed (for example, day, hour, minute, and second at which an input has been provided to indicate that the rehabilitation has been completed); and location information indicating the location at which the rehabilitation has been performed. Conversation data 1124 is associated with a space-time tag 1156. Space-time tag 1156 includes: time at which the conversation has been made (for example, day, hour, minute, and second at which an input has been provided to a tablet terminal of an attendant so as to indicate end of the conversation); and location information indicating the location which the conversation has been made.

Then, in sensor/camera 1130, video image data 1133 is associated with a space-time tag 1157. Space-time tag 1157 includes: time information indicating time (year, month, day, hour, minute, and second) at which video image data 1133 has been obtained; and location information indicating the location at which the video image data has been obtained. Video image data 1134 is associated with a space-time tag 1158. Space-time tag 1158 includes: time information indicating time (year, month, day, hour, minute and second) at which video image data 1134 has been obtained; and location information indicating the location at which the video image data has been obtained. It should be noted that the location information in each of space-time tags 1157, 1158 is based on, for example, data included in the signal transmitted by transmitter 131 provided in sensor/camera 1130 or transmitter 131 installed in the vicinity of sensor/camera 1130.

In information home appliance 1140, operation data 1143 is associated with a space-time tag 1159. Space-time tag 1159 includes: time information indicating time (year, month, day, hour, minute, and second) at which information home appliance 1140 has been operated; and location information indicating the location at which information home appliance 1140 has been operated. Operation data 1144 is associated with space-time tag 1160. Space-time tag 1160 includes: time information indicating time (year, month, day, hour, minute, and second) at which information home appliance 1140 has been operated; and location information indicating the location at which information home appliance 1140 has been operated. It should be noted that the location information included in each of space-time tags 1159, 1160 is based on a signal sent from transmitter 131 placed at the home of the user. Accordingly, even in the indoor where a positioning signal sent by GPS 160 is not received, location information can be obtained from transmitter 131.

In such circumstances, space-time ID 1100 is generated. Space-time ID 1100 is constituted of the plurality of space-time tags along a time line. Based on data authenticated by location information management server 110, space-time ID 1100 is generated by mobile communication terminal 100 or regional medical data bank system 120. More specifically, space-time ID 1100 includes space-time tags 1170 to 1180. Space-time tag 1170 is associated with user ID 1111 and the content of space-time tag 1150. Space-time tag 1171 is associated with examination data 1113 and the content of space-time tag 1151. Space-time tag 1172 is associated with treatment data 1114 and the content of space-time tag 1152. Space-time tag 1173 is associated with medication data 1115 and the content of space-time tag 1153. Space-time tag 1174 is associated with user ID 1121 and the content of space-time tag 1154. Space-time tag 1175 is associated with rehabilitation data 1123 and the contents of space-time tags 1153, 1155. Space-time tag 1176 is associated with conversation data 1124 and the content of space-time tag 1156. Space-time tag 1177 is associated with video image data 1133 and the content of space-time tag 1157. Space-time tag 1178 is associated with video image data 1134 and the content of space-time tag 1158. Space-time tag 1179 is associated with operation data 1143 and the content of space-time tag 1159. Space-time tag 1180 is associated with operation data 1144 and the content of space-time tag 1160.

Then, in regional medical data bank system 120, verification processing unit 124 verifies (i) track information constituted of respective pieces of location information stored in space-time information DB 122 against (ii) space-time tag 181 and medical information 182 stored in EHR information DB 123, thereby extracting personal record in a time series manner. For example, verification processing unit 124 verifies (i) location information and time information associated with each of the series of space-time tags constituting the space-time ID against (ii) space-time tag 181 transmitted from medical institution 130. When space-time tag 181 is included in the series of space-time tags, medical information 182 can be found to be medical information about the user of mobile communication terminal 100 having generated space-time tag 181.

[System Configuration]

Figure 12:
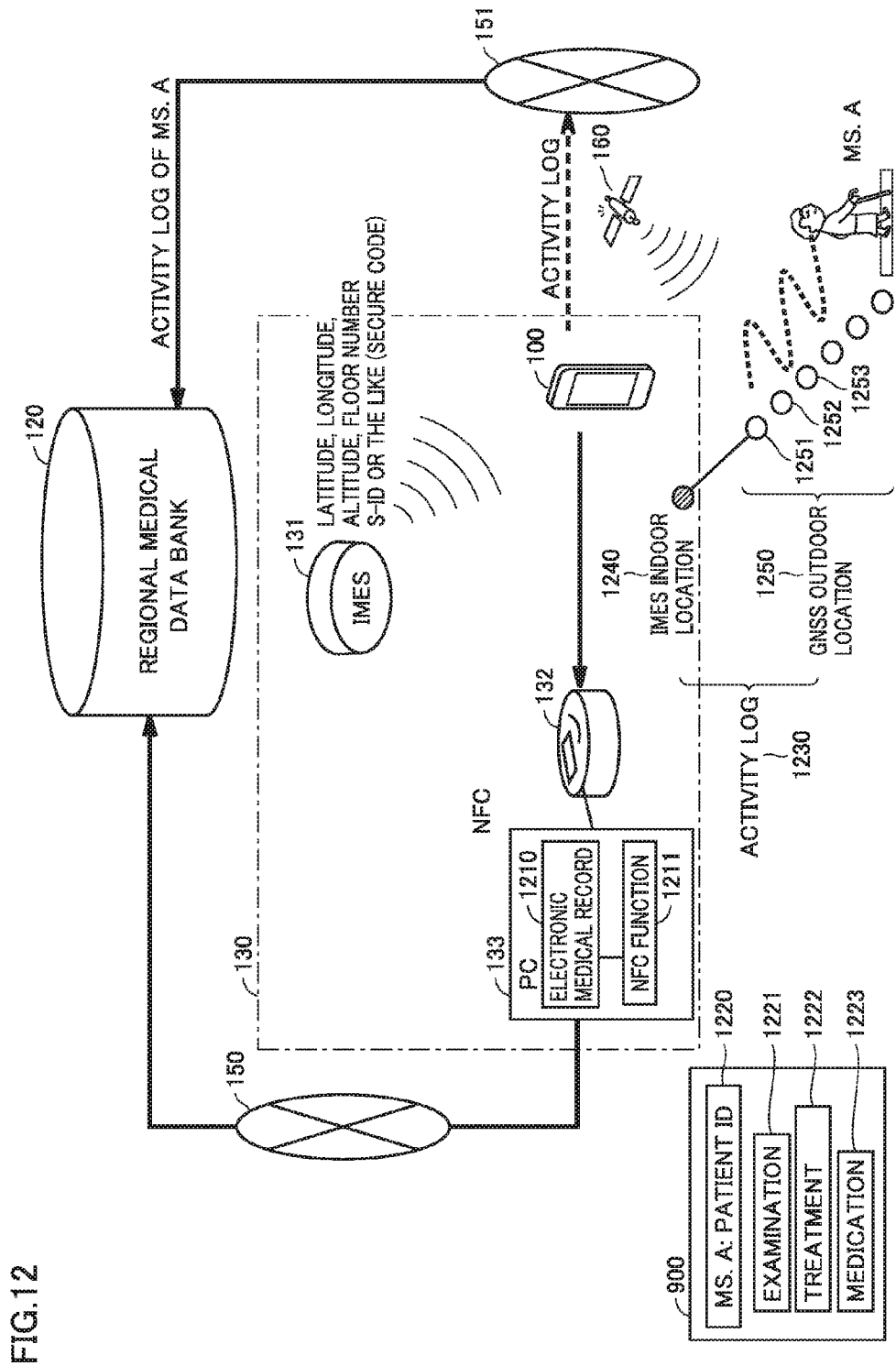
FIG. 12 shows an exemplary system configuration using a regional medical data bank system 120.

With reference to FIG. 12, the following describes a system configuration to which the technical idea according to the present embodiment is applied. FIG. 12 shows an exemplary system configuration that uses regional medical data bank system 120. In a certain aspect, regional medical data bank system 120 is connected to terminal device 133 via network 150. Moreover, regional medical data bank system 120 can communicate with mobile communication terminal 100 via a network 151. In medical institution 130, in addition to terminal device 133, transmitter 131 is installed on the ceiling of the consultation room. Furthermore, NFC terminal 132 is connected to terminal device 133.

In a certain aspect, a user (for example, Ms. A) of mobile communication terminal 100 goes to medical institution 130 and is subjected to medical diagnosis. On this occasion, transmitter 131 placed in the consultation room of medical institution 130 transmits a signal including location information. For example, the location information includes: latitude, longitude, altitude, floor number, or the like; and a secure code. The secure code is a code previously assigned to transmitter 131 to indicate that the signal itself is valid. Mobile communication terminal 100 receives the signal transmitted by transmitter 131, and obtains location information included in the signal. The location information obtained on this occasion is stored in a memory of mobile communication terminal 100 as an IMES indoor location 1240, for example.

Then, when the user goes from medical institution 130 to outside, mobile communication terminal 100 receives positioning signals transmitted by GPS 160. Mobile communication terminal 100 obtains the location based on positioning signals transmitted from four GPS satellites 160, for example. The location obtained on this occasion is stored in the memory of mobile communication terminal 100 as GNSS outdoor location 1250, for example. Likewise, while the user is walking outside, the location of the user is obtained for every period of time set in advance. The location obtained is held in the memory as GNSS outdoor locations 1251, 1252, 1253, for example.

In medical institution 130, in response to touch to NFC terminal 132, mobile communication terminal 100 transmits, to terminal device 133, (i) the location information (latitude, longitude, altitude, or floor number) and the secure code both received at the location and (ii) the terminal ID of mobile communication terminal 100. Terminal device 133 generates a space-time ID based on the location information received from mobile communication terminal 100. Further, terminal device 133 adds the space-time ID to medical information. Terminal device 133 transmits the medical information having the space-time ID added thereto to regional medical data bank system 120.

[Generation and Utilization of Space-Time ID]

Figure 13:
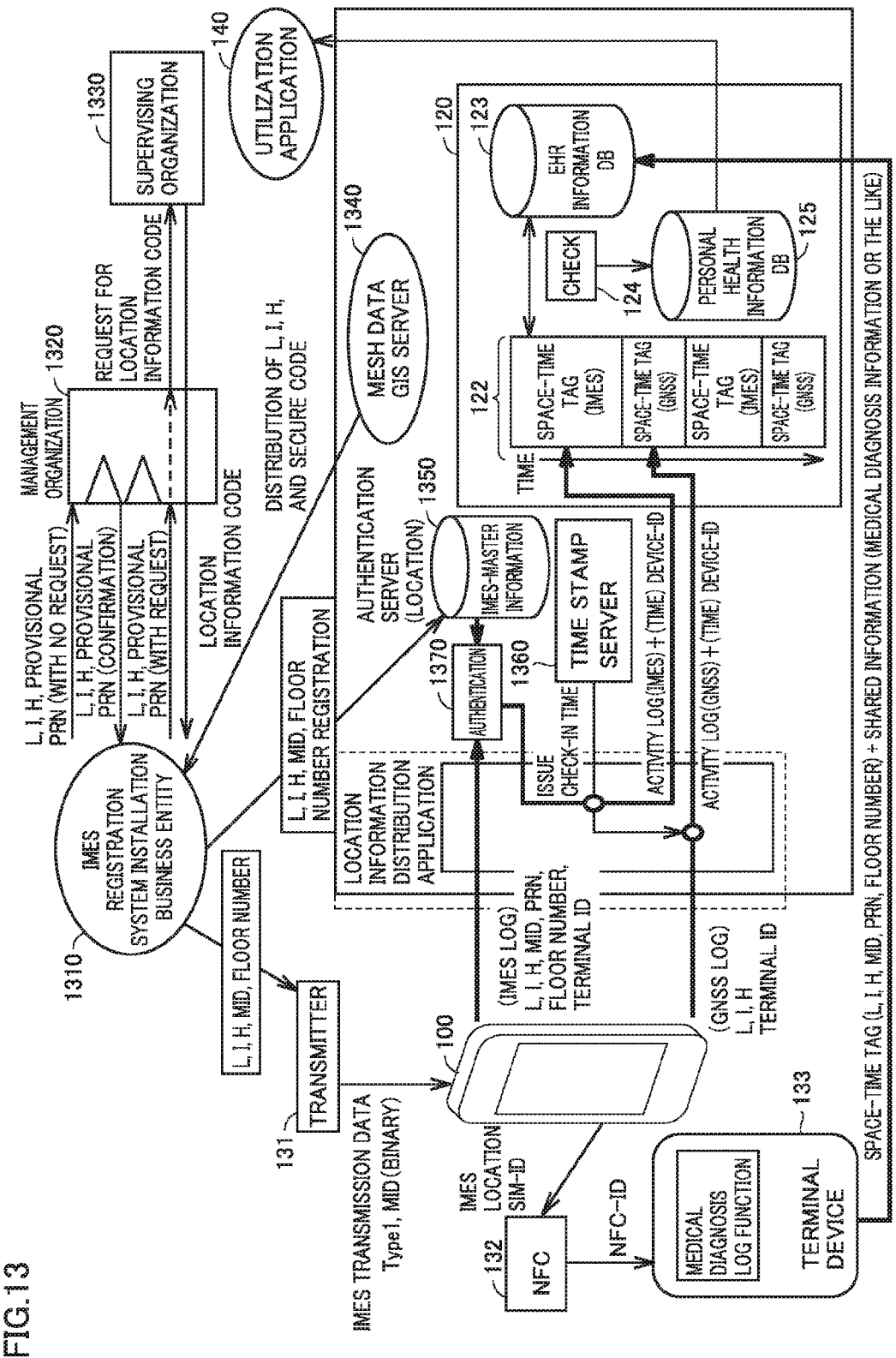
FIG. 13 shows one manner of generation and utilization of the space-time ID.

With reference to FIG. 13, the following describes generation and utilization of the space-time ID according to the present embodiment. FIG. 13 shows one manner of generation and utilization of the space-time ID. In a certain aspect, an IMES registration system installation business entity 1310 distributes location information (latitude, longitude, altitude, and the like) and secure code to a mesh data GIS (Geographic Information System) server 1340. Mesh data GIS server 1340 is configured to provide geographic information.

IMES registration system installation business entity 1310 transmits the location information and a provisional PRN (with no request) to a management organization 1320. Management organization 1320 is an organization involved in management of an organization responsible for emitting a positioning signal, for example. Management organization 1320 transmits location information (latitude L, longitude I, altitude H) and PRN (confirmation) to IMES registration system installation business entity 1310. Further, in another aspect, IMES registration system installation business entity 1310 transmits location information and a provisional PRN (with request) to a supervising organization 1330 via management organization 1320. Management organization 1320 requests supervising organization 1330 for a location information code. Supervising organization 1330 distributes the requested location information code to IMES registration system installation business entity 1310. Supervising organization 1330 is the Geographical Survey Institute, for example.

In another aspect, IMES registration system installation business entity 1310 transmits the location information (L, I, H, MID, floor number) to transmitter 131, and transmitter 131 writes the received data in a memory area defined in advance. IMES registration system installation business entity 1310 transmits the location information (L, I, H, MID, floor number) to an authentication server 1350. Authentication server 1350 holds the data as IMES-master information. Transmitter 131 transmits a signal including a location within a range (for example, radius of 1 m, 2 m or the like) defined in advance. The signal is defined by type 1 and MID (binary) as IMES transmission data, for example. When mobile communication terminal 100 is within such a range, mobile communication terminal 100 receives such a signal to obtain the location information.

Mobile communication terminal 100 transmits the location information and the terminal ID to location information management server 110 as an IMES log. Location information management server 110 performs an authenticating process 159 using (i) the IMES log sent from mobile communication terminal 100 and (ii) the data stored in authentication server 1350. The result of authentication is associated with a time stamp output by time stamp server 1360. Furthermore, the result of authentication is also transmitted to regional medical data bank system 120.

On the other hand, when the positioning signal transmitted by GPS 160 can be received, mobile communication terminal 100 transmits location information (latitude, longitude, and altitude) and terminal ID to location information management server 110 as a GNSS log. The timing of transmission is not particularly limited. Location information management server 110 associates check-in time output from time stamp server 1360 with the GNSS log, and transmits the associated data to regional medical data bank system 120. Each piece of the data is stored in space-time ID information DB 122 as a space-time tag (GNSS). In regional medical data bank system 120, the space-time tag is stored in a file created for each user. Each file includes: terminal identification information; user name; space-time tag (location information+time information); the version number of map data when the location information has been obtained; and the like. A series of space-time tags can constitute a space-time ID.

In regional medical data bank system 120, a process by check processing unit 124 is applied to space-time ID information DB 122 and EHR information DB 123. The result of process by check processing unit 124 is stored in personal health information DB 125. Further, in a certain aspect, the data stored in personal health information DB 125 is appropriately used by utilization application 140. Utilization application 140 may be used by a health insurance institution or other business entities that provide medical services, for example.

On the other hand, mobile communication terminal 100 transmits the location information (IMES location) to terminal device 133 via NFC terminal 132. NFC terminal 132 transmits, to terminal device 133, data in which an NFC-ID is provided to the signal received from mobile communication terminal 100. In a certain aspect, terminal device 133 has a medical diagnosis information log function and can sequentially record respective pieces of medical diagnosis information of patients. In another aspect, terminal device 133 transmits a space-time ID (L, I, H, MID, PRN, floor number) and common information (such as diagnosis information) to EHR information DB 123 of regional medical data bank system 120. EHR information DB 123 holds the information.

[Configuration of Database]

Figure 14:
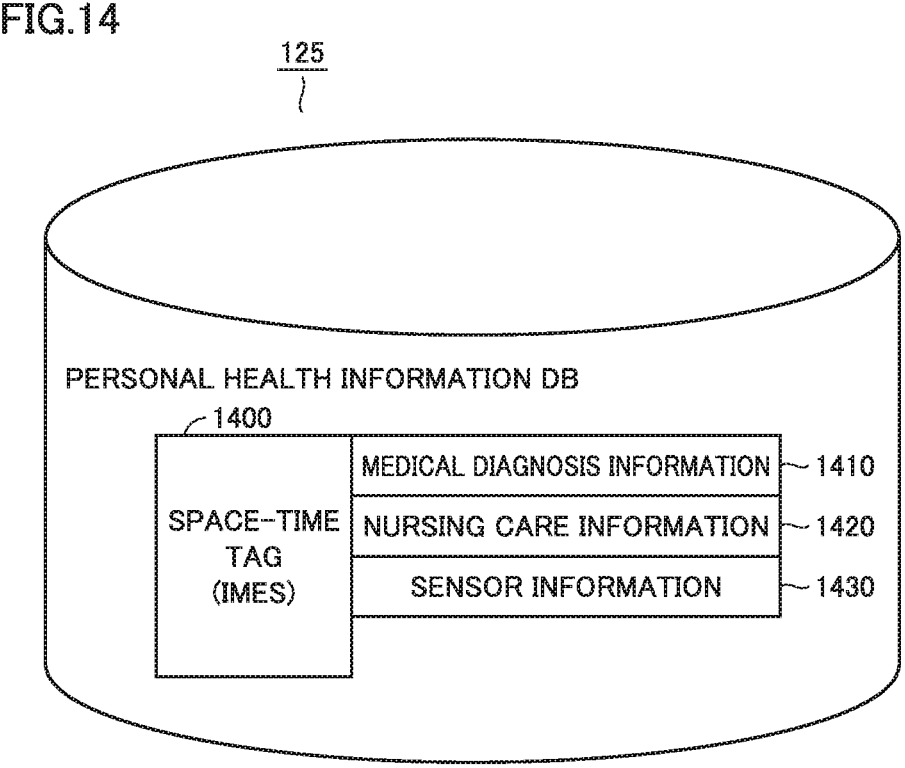
FIG. 14 conceptually shows one manner of storing data in a personal health information DB 125 according to the embodiment of the present invention.

FIG. 14 conceptually shows one manner of storing data in personal health information DB 125 according to the embodiment of the present invention. In a certain aspect, personal health information DB 125 stores a plurality of space-time tags. One space-time tag 1400 is associated with medical diagnosis information 1410, nursing care information 1420, and sensor information 1430. Hence, when space-time tag 1400 is specified, medical diagnosis information 1410, nursing care information 1420, and sensor information 1430 are specified.

[Control Structure]

Figure 15:
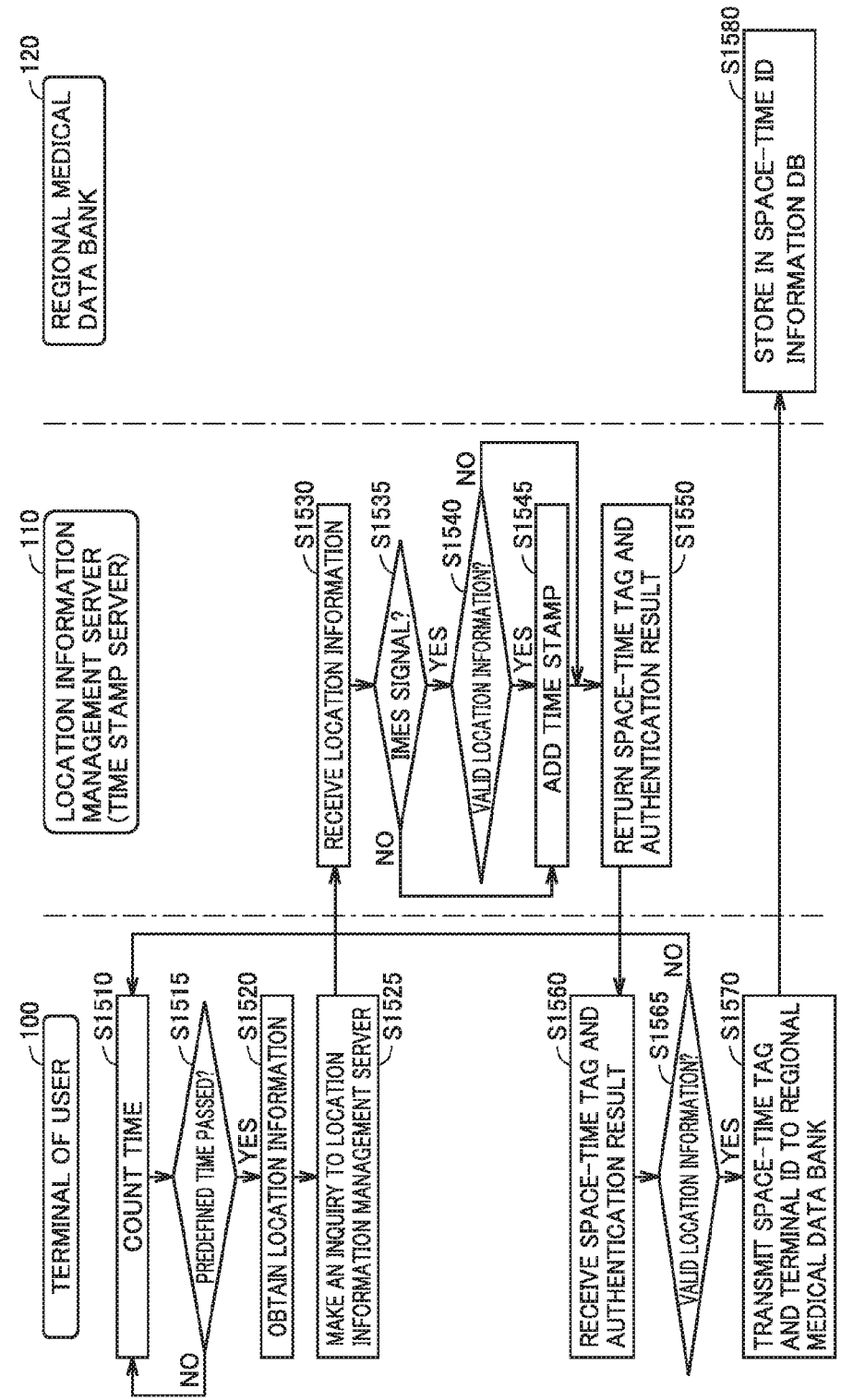
FIG. 15 is a flowchart showing a registration process for activity log.
Figure 16:
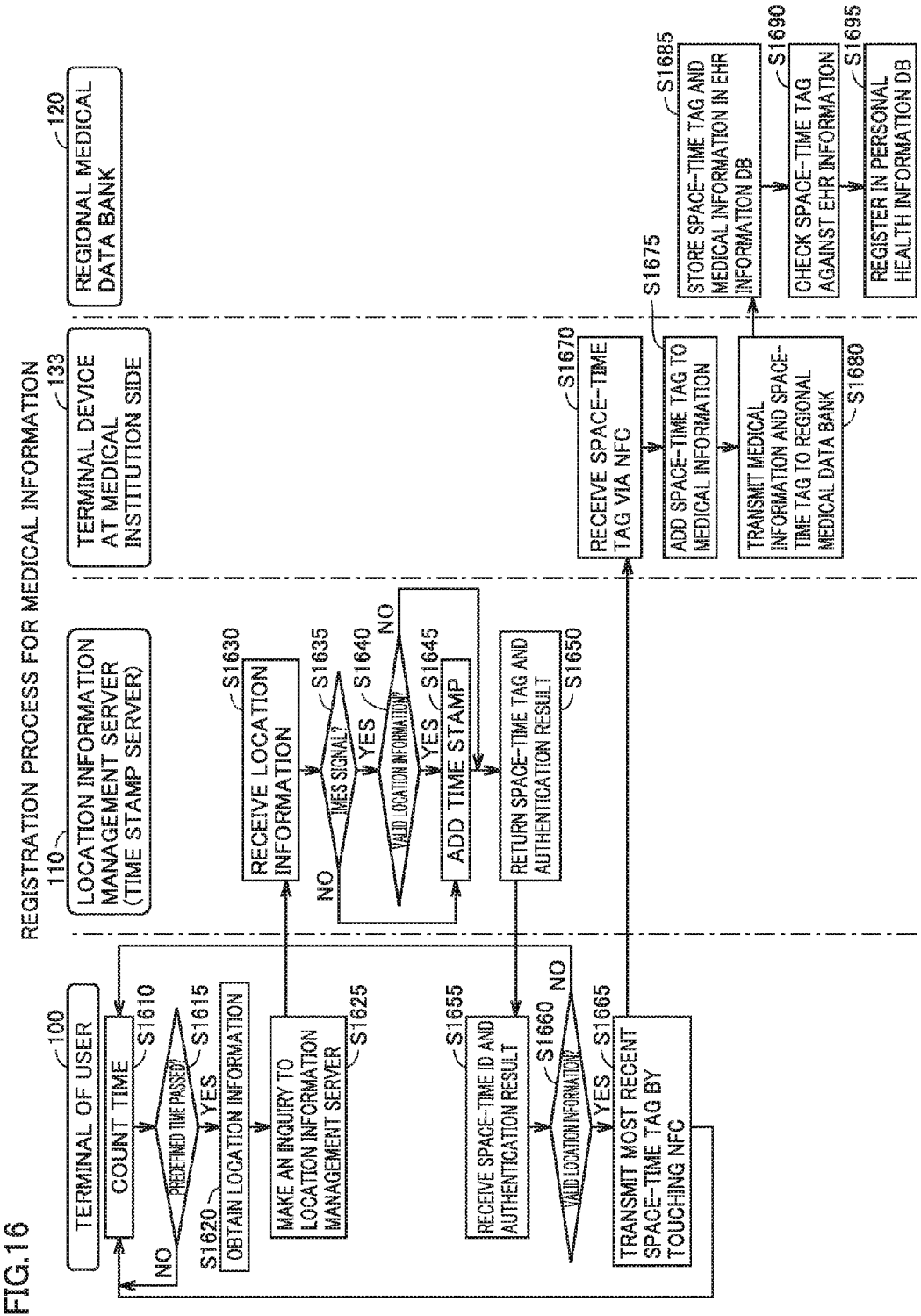
FIG. 16 is a flowchart showing a registration process for medical information.
Figure 17:
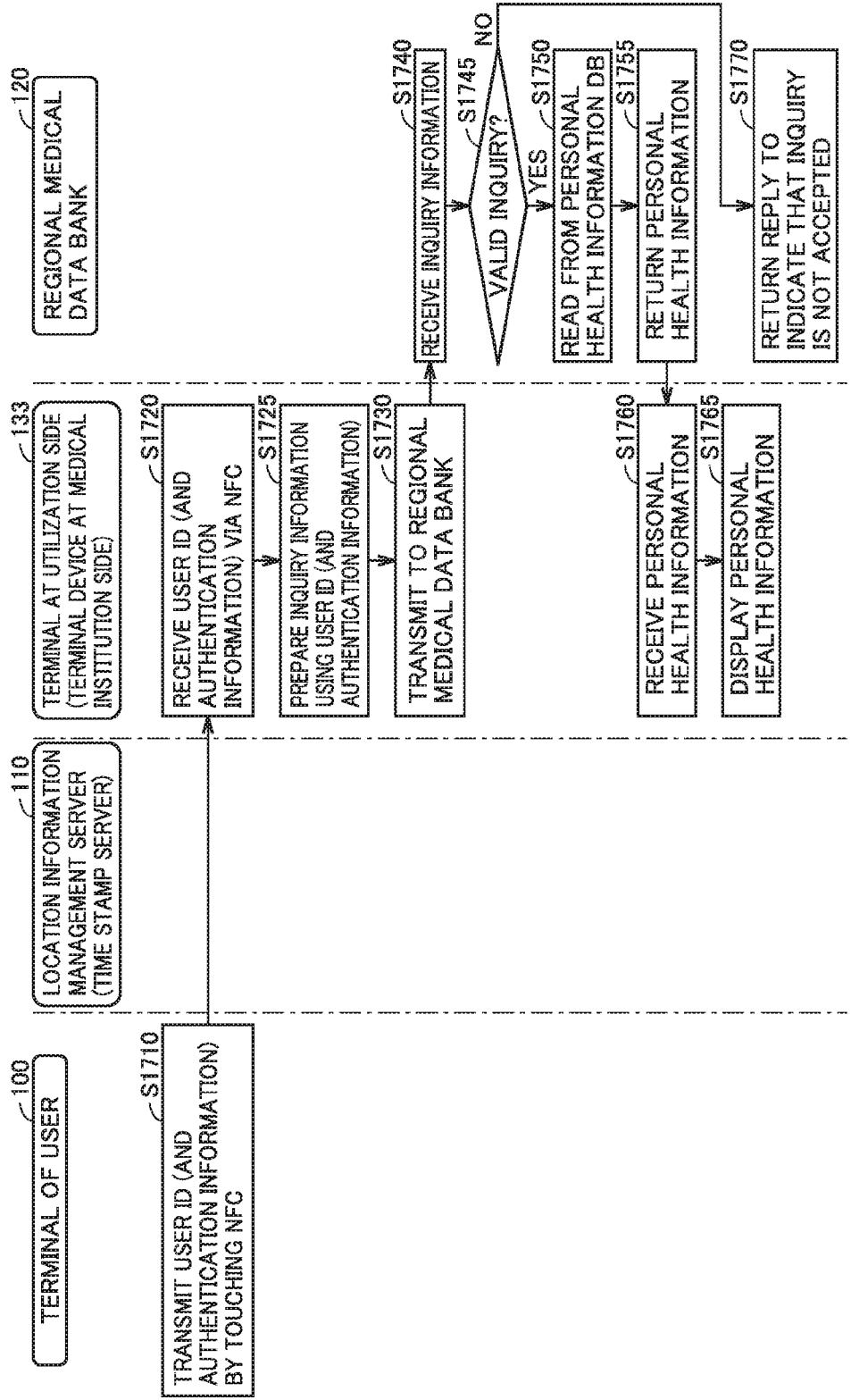
FIG. 17 is a flowchart showing a utilization process for personal health information.

With reference to FIG. 15 to FIG. 17, the following describes a control structure in the present embodiment. FIG. 15 is a flowchart showing a registration process for activity log. FIG. 16 is a flowchart indicating a registration process for medical information. FIG. 17 is a flowchart indicating a utilization process for personal health information.

[Registration Process for Activity Log]

With reference to FIG. 15, in a step S1510, CPU 50 of mobile communication terminal 100 of the user counts time. For example, the count of time is performed based on a signal from a clock included in mobile communication terminal 100. In a step S1515, CPU 50 determines whether or not a predefined time from the start of count has passed. When CPU 50 determines that the predefined time has passed (YES in step S1515), CPU 50 switches the control to a step S1520. Otherwise (NO in step S1515), CPU 50 returns the control to step S1510. In step S1520, CPU 50 obtains location information. In a step S1525, CPU 50 makes an inquiry to location information management server 110.

In a step S1530, CPU 1 of location information management server 110 receives the location information from mobile communication terminal 100. In a step S1535, CPU 1 determines whether or not the received signal is an IMES signal. This determination is performed based on an item (for example, PRN-ID) included in the signal received from mobile communication terminal 100. When CPU 1 determines that the received signal is an IMES signal (YES in step S1535), CPU 1 switches the control to a step S1540. Otherwise (NO in step S1535), CPU 1 switches the control to a step S1545.

In step S1540, CPU 1 determines whether or not the location information included in the signal received from mobile communication terminal 100 is valid location information. When CPU 1 determines that the location information is valid location information (YES in step S1540), CPU 1 switches the control to step S1545. Otherwise (NO in step S1540), CPU 1 switches the control to a step S1550. In step S1545, CPU 1 provides a time stamp to the location information. In step S1545, to mobile communication terminal 100, CPU 1 returns the space-time tag, which has the location information and the time information, and the authentication result.

In a step S1560, CPU 50 of mobile communication terminal 100 receives the space-time tag and the authentication result from location information management server 110. In a step S1565, CPU 50 determines whether or not the obtained location information is valid location information. For example, when CPU 50 determines that the location information is valid location information (YES in step S1565), CPU 50 switches the control to a step S1570. Otherwise (NO in step S1565), the control is returned to step S1510. In step S1570, CPU 50 transmits the space-time tag and the terminal ID of mobile communication terminal 100 to regional medical data bank system 120.

In a step S1580, CPU 1 of regional medical data bank system 120 stores, in space-time ID information DB 122, the space-time tag and terminal ID received from mobile communication terminal 100. A format for storing the data is not limited particularly. The configuration of the database may be at least a multi-dimensional database model format such as a cache.

[Registration Process for Medical Information]

With reference to FIG. 16, in a step S1610, CPU 50 of mobile communication terminal 100 determines whether or not a predefined time has passed. When CPU 50 determines that the predefined time has passed (YES in step S1615), CPU 50 switches the control to step S620. Otherwise (NO in step S1615), CPU 50 returns the control to step S1610. In step S1620, CPU 50 obtains the location information. In step S1625, CPU 50 makes an inquiry to location information management server 110.

In a step S1630, CPU 1 of location information management server 110 receives the location information transmitted from mobile communication terminal 100. In a step S1635, CPU 1 determines whether or not the signal is an IMES signal. As with the above determination, this determination is performed based on the item included in the IMES signal. When CPU 1 determines that the signal is an IMES signal (YES in step S1635), CPU 1 switches the control to a step S1640. Otherwise (NO in step S1635), CPU 1 switches the control to a step S1645.

In step S1640, CPU 1 determines whether or not the information included in the signal is valid location information. When CPU 1 determines that the location information is valid information (YES in step S1640), CPU 1 switches the control to step S1645. Otherwise (NO in step S1640), CPU 1 switches the control to a step S1650. In step S1645, CPU 1 provides a time stamp (time information) to the location information. In step S1650, to mobile communication terminal 100, CPU 1 returns the space-time tag, which has the location information and the time information, and the authentication result.

In a step S1655, CPU 50 of mobile communication terminal 100 receives the space-time tag and the authentication result from location information management server 110. In a step S1660, CPU 50 determines whether or not the location information is valid location information. When CPU 50 determines that the location information is valid location information (YES in step S1660), CPU 1 switches the control to a step S1665. Otherwise (NO in step S1660), CPU 50 returns the control to step S1610. In step S1665, in response to touch on NFC, CPU 50 transmits the most recent space-time tag to terminal device 133.

In a step S1670, CPU 1 of terminal device 133 receives the space-time tag from mobile communication terminal 100 via the NFC. In a step S1675, CPU 1 generates a data set having the space-time tag added to medical information (for example, medical diagnosis result, vital data, or the like). In a step S1680, CPU 1 transmits, to regional medical data bank system 120, the medical information having the space-time tag added thereto.

In a step S1685, in regional medical data bank system 120, CPU 1 of server 120B stores, in EHR information DB 123, the information received from terminal device 133. In a step S1690, CPU 1 performs verification by checking the space-time tag stored in space-time ID information DB 122 against the space-time tag stored in the EHR information DB. When the result of verification is OK, in a step S1695, CPU 1 registers the space-time tag in personal health information DB 125. When the result of verification is NG, CPU 1 can notify terminal device 133 that the space-time tag cannot be registered.

[Utilization Process for Personal Health Information]

With reference to FIG. 17, the following describes a process when personal health information is to be used. When utilization of the health information is requested, this process is performed by a switch (not shown) connecting server 120A and server 120B to each other. Therefore, health information of an individual person is protected even if invalid access to regional medical data bank system 120 is performed.

In a step S1710, in response to touch on NFC terminal 132, CPU 50 of mobile communication terminal 100 transmits the user ID and authentication information of mobile communication terminal 100 to terminal device 133.

In a step S1720, CPU 1 of terminal device 133 receives, via NFC terminal 132, the user ID and authentication information transmitted from mobile communication terminal 100. In a step S1725, CPU 1 prepares inquiry information using the user ID and the authentication information. In a step S1730, CPU 1 of terminal device 133 transmits the inquiry information to regional medical data bank system 120.

In a step S1740, in regional medical data bank system 120, CPU 1 of server 120B receives the inquiry information sent from terminal device 133. In a step S1745, CPU 1 determines whether or not the inquiry information is a valid inquiry. When CPU 1 determines that the inquiry information represents a validate inquiry (YES in step S1745), CPU 1 switches the control to a step S1750. Otherwise (NO in step S1745), CPU 1 switches the control to a step S1770.

In step S1750, server 120B transmits a connection request to server 120A. In response to the connection request, server 120A turns the switch to establish connection between server 120A and server 120B. When server 120A and server 120B are connected to each other, CPU 1 reads space-time ID constituted of a series of space-time tags stored in space-time ID information DB 122, and reads, from personal health information DB 125, personal health information corresponding to the inquiry information. In a step S1755, CPU 1 of server 120B transmits the read personal health information to terminal device 133.

In a step S1760, CPU 1 of terminal device 133 receives the personal health information transmitted from regional medical data bank system 120. In a step S1765, CPU 1 of terminal device 133 displays the personal health information on monitor 8. In step S1770, CPU 1 of server 120B returns a reply to terminal device 133 to indicate that the inquiry is not accepted.

It should be noted that in another aspect, personal medical information and other service information may be obtained also through utilization terminal 141. For example, when utilization terminal 141 has the NFC function, utilization terminal 141 receives the user ID and the space-time tag (location information and time information) from mobile communication terminal 100 in response to the touch of mobile communication terminal 100. Utilization terminal 141 transmits, to server 120B, a PHR-ID associated with the user ID, thereby requesting personal medical information. Server 120B verifies the received PHR-ID against a PHR-ID stored in regional medical data bank system 120 to determine whether or not the request is a valid request. When the request is a valid request, server 120B transmits a connection request to server 120A. Verification processing unit 124 checks whether or not the space-time tag sent from utilization terminal 141 to server 120B is included in the series of space-time tags stored in space-time ID information DB 122 of server 120A. When the space-time tag is included in the series of space-time tags, server 120B reads, from personal health information DB 125, the health information associated with the space-time tag and transmits it to utilization terminal 141.

In this way, the activity log and medical information are registered in regional medical data bank system 120, whereby the personal health information is used. The data is recorded using the space-time tag and is utilized to verify whether or not the medical information, the medical diagnosis information, and the like stored in the database are valid information, thereby securing validness of the request made based on the personal information. Moreover, since server 120A and server 120B are connected to each other when a valid request is made, information stored in personal health information DB 125 can be prevented from being leaked.

[Conclusion of Embodiment]

With reference to FIG. 18, the following describes details of the configuration of a space-time tag 181. FIG. 18 shows an example of space-time tag 181 in a certain aspect. Space-time tag 181 includes a time stamp 1810, a latitude 1820, a longitude 1830, a URI 1840 (Uniform Resource Identifier), and an MIME 1850 (Multipurpose Internet Mail Extensions). Time stamp 1810 corresponds to time information obtained by satellite positioning, or time information obtained by a time stamp server that authenticates validness of the location information. Latitude 1820, longitude 1830, and altitude 1835 correspond to the location information obtained by satellite positioning, or the location information obtained by transmitter 131. For example, URI 1840 is information for making access to information provided by an institution having produced space-time tag 181. MIME 1850 is data associated with space-time tag 181, and corresponds to letter information, a still image, a motion image, or the like.

Figure 19:
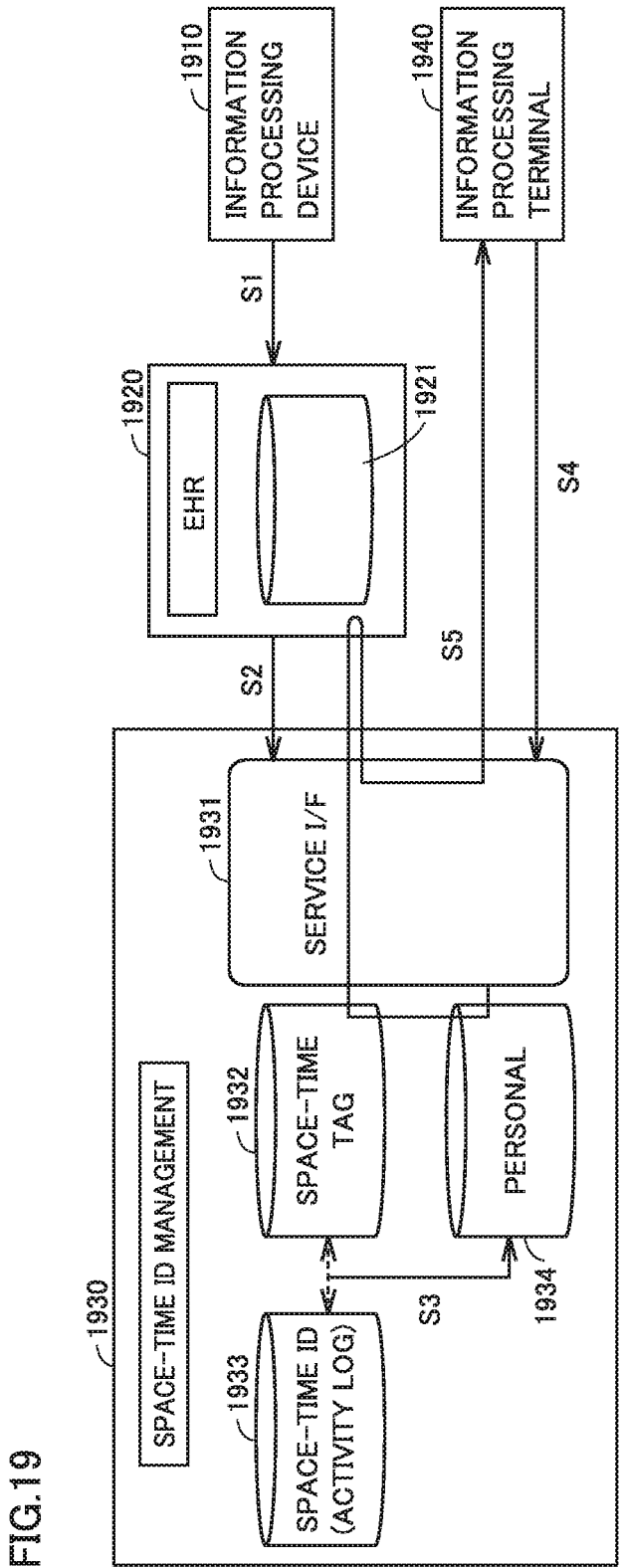
FIG. 19 conceptually shows an exemplary configuration of an information management system.

With reference to FIG. 19, data processing in the information management system will be described. FIG. 19 conceptually shows an exemplary configuration of the information management system. The information management system includes an information processing device 1910, an EHR information DB 1920, a space-time ID management system 1930, and an information processing terminal 1940. Space-time ID management system 1930 includes a service interface 1931, a space-time tag DB 1932, a space-time ID 1933, and a personal information DB 1934.

For example, information processing device 1910 is an electronic health record system or a different device, and outputs specific information (for example, other examination result and EHR data) to each user (for example, patient) who receives medical service or another service (step S1). EHR information DB 1920 imports the EHR data and generates a space-time tag by associating the time information and the location information with the EHR data. Information processing device 1910 transmits the space-time tag to space-time ID management system 1930 (step S2).

Space-time ID management system 1930 imports each space-time tag via service interface 1931, and stores it in space-time tag DB 1932. Space-time ID DB 1933 reads a series of space-time tags from space-time tag DB 1932. Space-time ID DB 1933 constructs personal identification information using the series of space-time tags as a space-time ID. Personal information DB 1934 holds information (PHR) provided to an individual person, such as medical information, nursing care information and other information.

On the other hand, information processing terminal 1940 executes an application to request space-time ID management system 1930 for personal information (step S4). In response to the request, space-time ID management system 1930 verifies (i) the space-time tag included in the request sent from information processing terminal 1940 against (ii) the space-time tag included in space-time ID stored in space-time tag DB 1932, so as to determine whether or not the request for personal information is valid (step S3). When space-time ID management system 1930 determines that the request for personal information is valid as a result of the verification process, space-time ID management system 1930 reads, from EHR information DB 1920, data to be referenced by a URI included in the space-time tag included in the space-time ID, and space-time ID management system 1930 reads the PHR from personal information DB 1934. Service I/F 1931 transmits the read data or PHR to information processing terminal 1940 (step S5).

Figure 20:
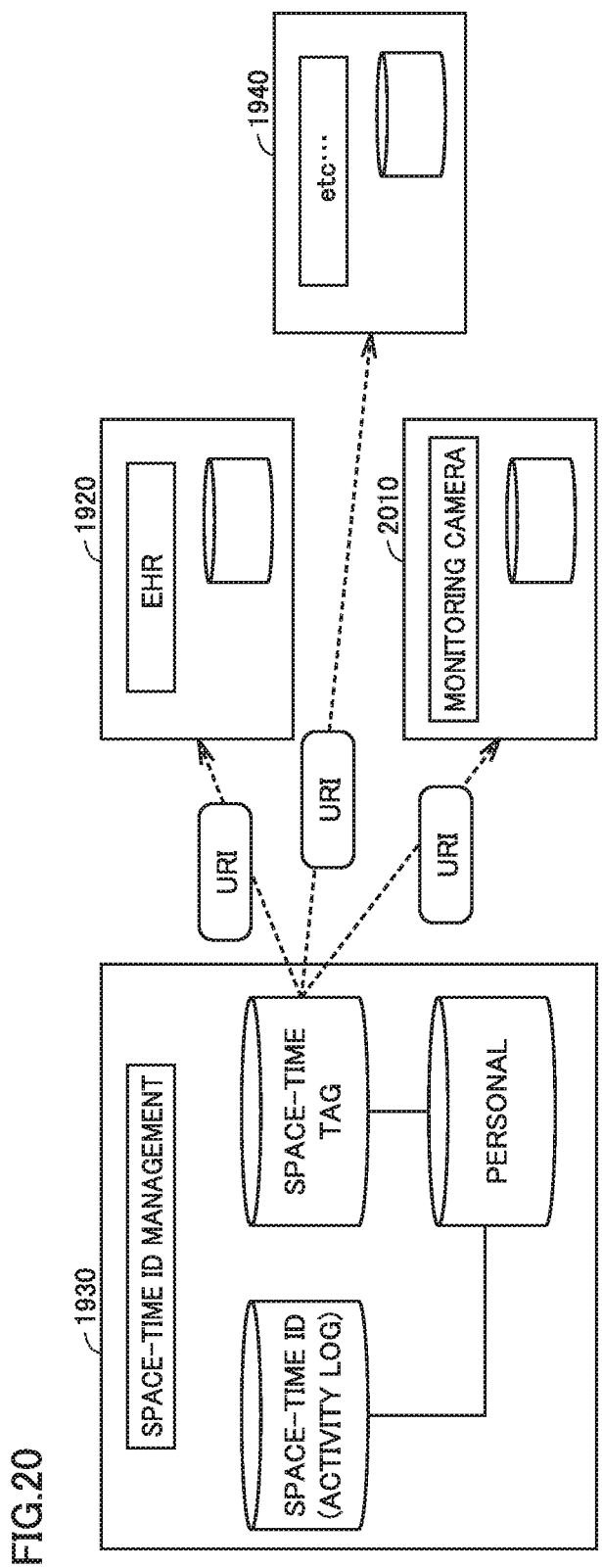
FIG. 20 shows an overview of the configuration of the information management system.

With reference to FIG. 20, the following describes another configuration of the information management system. FIG. 20 shows an overview of the configuration of the information management system. The information management system according to the present embodiment is not limited to the above-described configuration. As shown in FIG. 20, the information management system includes a monitoring camera system 2010 in addition to the configuration shown in FIG. 19. Monitoring camera system 2010 includes a camera and a memory for holding an image. Monitoring camera system 2010 can be connected with the Internet or other networks. A URI is assigned to monitoring camera system 2010. Space-time ID management system 1930 can receive a URI associated with the space-time tag sent from monitoring camera system 2010. Hence, space-time ID management system 1930 can make reference to the URI to access an image obtained by monitoring camera system 2010. In this case, the image is associated with the space-time data, and is not associated with personal information such as a name, for example. Accordingly, personal information is not specified from the image.

As fully described in detail above, for provision of medical services, a patient holds a mobile terminal such as a smartphone or a different terminal, records (logs) location information at a regular interval, and transmits the location information to regional medical data bank system 120. On the other hand, for every activity for which direct permission from the patient is obtained by NFC, a medical service provider adds the location information of the location (such as medical institution 130) and the time information (i.e., space-time ID) to the information (medical information) necessary for medical analysis among expense claim data (medical receipt information) used for medical expense claims, and transmits the medical information to regional medical data bank system 120. In regional medical data bank system 120, both the space-times ID are verified (checked) against each other, thereby collecting medical information for each patient. A space-time ID can be readily added to medical information or health information obtained from not only a PC used in a medical institution but also a terminal used by a nursing care service provider, an insurance service provider or the like, a television, a camera, a cleaning robot, and other information home appliances. In this way, a new structure for information sharing can be provided in the medical industry and other industries in which information sharing must be facilitated in a wide range.

Moreover, since personal information can be identified without using a conventional personal ID, an individual person associated with information of a space-time tag cannot be specified even if data included in the space-time tag is leaked. Accordingly, a protection level of personal information is improved. As a result, a structure for protecting information such as VPN (Virtual Private Network) becomes unnecessary, thereby reducing investment in systematization, for example.

The embodiments disclosed herein are illustrative and non-restrictive in any respect. The scope of the present invention is defined by the terms of the claims, rather than the embodiments described above, and is intended to include any modifications within the scope and meaning equivalent to the terms of the claims.

REFERENCE SIGNS LIST

1: CPU; 2: mouse; 3: keyboard; 4, 55, 430: RAM; 5: hard disk; 6: optical disk driving device; 7, 63, 66: communication I/F; 8: monitor; 9: CD-ROM; 10: information management system; 51: communication device; 52: switch; 53, 1130: camera; 54: flash memory; 56, 440: ROM; 57: memory card driving device; 58, 170: microphone; 59: audio signal processing circuit; 60: speaker; 61, 350, 640: display; 62: LED; 64: vibrator; 65: secondary battery; 67, 71, 492, 602: antenna; 68: positioning signal receiving front end unit; 69: positioning processing unit; 70: memory card; 100: mobile communication terminal; 110: location information management server; 120: regional medical data bank system; 121: space-time ID information processing unit; 122, 123, 1685: information DB; 124: check processing unit; 125: personal health information DB; 130: medical institution; 131, 311, 312, 313, 314: transmitter; 132: terminal; 133: terminal device; 140: utilization application; 141: utilization terminal; 150, 151: network; 159: authentication process; 160: satellite; 171: location information log; 180, 1142: information; 181: space-time tag; 182: medical information; 270: external clock; 410: digital processing block; 422: code pattern; 460: digital input/output interface; 480: clock; 490: analog processing block; 494: power source; 604: front circuit; 606: down converter; 608: converter; 610: baseband processor; 612: correlator unit; 614: control unit; 616: determining unit; 620: memory; 630: navigation processor; 632: outdoor positioning unit; 634: indoor positioning unit; 800: computer; 1310: registration system installation business entity; 1320: management organization; 1330: supervising organization; 1340: server; 1350: authentication server; 1360: time stamp server.

What is claimed is:

1. An information management system comprising:
a plurality of mobile communication terminals each capable of obtaining location information;
a data bank device for managing a database of each user of the plurality of mobile communication terminals; and
a service information management device for transmitting service information to the data bank device, the service information being associated with a service provided to a user of a specific mobile communication terminal of the plurality of mobile communication terminals,
each of the mobile communication terminals including
an obtaining unit configured to obtain identification information including a set of location information for specifying a location of the mobile communication terminal and time information, and
a first transmitting unit configured to transmit a plurality of pieces of the identification information to the data bank device and the service information management device,
the service information management device including
a receiving unit configured to receive the identification information from the specific mobile communication terminal, and
a second transmitting unit configured to transmit, to the data bank device, the service information and identification information received from the specific mobile communication terminal,
the data bank device including
a receiving unit configured to receive the identification information transmitted by each of the plurality of mobile communication terminals and the identification information and service information transmitted by the service information management device, and a verifying unit configured to verify each piece of the received identification information to specify a user having been provided with a service associated with the service information.

2. The information management system according to claim 1, wherein
in the mobile communication terminal, the obtaining unit includes:
a first positioning unit configured to obtain location information of the mobile communication terminal and time based on respective positioning signals transmitted from a plurality of positioning satellites; and
a second positioning unit configured to receive a signal including location information indicating a location of a location information transmitting device from the location information transmitting device, extract the location information from the received signal, and obtain time associated with the location information, the location information transmitting device being capable of transmitting a signal in a same format as a format of each of the positioning signals transmitted from the plurality of positioning satellites.

3. The information management system according to claim 2, wherein from a device other than the location information transmitting device, the second positioning unit is configured to obtain the time associated with the location information extracted by the second positioning unit.

4. The information management system according to claim 2, wherein
the information management system further includes an authentication device for authenticating the identification information obtained by each of the mobile communication terminals, and
the authentication device includes
a receiving unit configured to receive, from each of the mobile communication terminals, the location information extracted by the second positioning unit,
a determining unit configured to check whether or not the received location information is valid location information, and
a time adding unit configured to, when the received location information is valid location information, add time information to the location information received from each of the mobile communication terminals and return the location information having the time information added thereto to the mobile communication terminal having transmitted the location information.

5. The information management system according to claim 1, wherein the first transmitting unit is configured to transmit the identification information to the service information management device based on approval by the user of the mobile communication terminal.

6. The information management system according to claim 1, wherein the obtaining unit is configured to obtain a plurality of pieces of the location information at a predetermined interval.

7. The information management system according to claim 1, wherein the obtaining unit is configured to obtain the location information when the mobile communication terminal is present in a range registered in advance.

8. A mobile communication terminal comprising:
an obtaining unit configured to obtain identification information including a set of location information for specifying a location of the mobile communication terminal and time information; and
a transmitting unit configured to transmit a plurality of pieces of the identification information to a data bank device for managing a database of a user of the mobile communication terminal and to a service information management device for transmitting, to the data bank device, service information associated with a service provided to the user, wherein
the obtaining unit includes
a first positioning unit configured to obtain location information of the mobile communication terminal and time based on respective positioning signals transmitted from a plurality of positioning satellites, and
a second positioning unit configured to receive a signal including location information indicating a location of a location information transmitting device from the location information transmitting device, extract the location information from the received signal, and obtain time associated with the location information, the location information transmitting device being capable of transmitting a signal in a same format as a format of each of the positioning signals transmitted from the plurality of positioning satellites.

9. The mobile communication terminal according to claim 8, wherein the transmitting unit is configured to transmit the identification information to the service information management device based on approval by the user of the mobile communication terminal.

10. The mobile communication terminal according to claim 8, wherein the obtaining unit is configured to obtain a plurality of pieces of the location information at a predetermined interval.

11. The mobile communication terminal according to claim 8, wherein when the mobile communication terminal is present in a range registered in advance, the obtaining unit is configured to obtain the location information.

12. A method for managing information, comprising:
providing a plurality of mobile communication terminals each capable of obtaining location information;
providing a data bank device for managing a database of each user of the plurality of mobile communication terminals;
providing a service information management device for transmitting service information to the data bank device, the service information being associated with a service provided to a user of a specific mobile communication terminal of the plurality of mobile communication terminals;
obtaining, by each of the plurality of mobile communication terminals, identification information including a set of location information for specifying a location of the mobile communication terminal and time information;
transmitting, by each of the plurality of mobile communication terminals, a plurality of pieces of the identification information to the data bank device and the service information management device;
receiving, by the service information management device, the identification information from the specific mobile communication terminal;
transmitting, by the service information management device, to the data bank device, the service information and identification information received from the specific mobile communication terminal,
receiving, by the data bank device, the identification information transmitted by each of the plurality of mobile communication terminals and the identification information and service information transmitted by the service information management device; and verifying, by the data bank device, each piece of the received identification information to specify a user having been provided with a service associated with the service information.

13. A method for communication, comprising:

obtaining identification information including a set of location information for specifying a location of a mobile communication terminal and time information; and transmitting a plurality of pieces of the identification information to a data bank device for managing a database of a user of the mobile communication terminal and to a service information management device for transmitting, to the data bank device, service information associated with a service provided to the user, wherein the obtaining includes:

obtaining location information of the mobile communication terminal and time based on respective positioning signals transmitted from a plurality of positioning satellites;

receiving a signal including location information indicating a location of a location information transmitting device from the location information transmitting device;

extracting the location information from the received signal; and obtaining time associated with the location information, the location information transmitting device being capable of transmitting a signal in a same format as a format of each of the positioning signals transmitted from the plurality of positioning satellites.

14. The method according to claim 13, wherein the transmitting includes transmitting the identification information to the service information management device based on approval by the user of the mobile communication terminal.

15. The method according to claim 13, wherein the obtaining identification information includes obtaining a plurality of pieces of the location information at a predetermined interval.

16. The method according to claim 13, wherein when the mobile communication terminal is present in a range registered in advance, the obtaining includes obtaining the location information.

* * * * *